United States Patent [19]

Weissmann

[11] Patent Number: 4,530,901

[45] Date of Patent: Jul. 23, 1985

[54] RECOMBINANT DNA MOLECULES AND THEIR USE IN PRODUCING HUMAN INTERFERON-LIKE POLYPEPTIDES

[75] Inventor: Charles Weissmann, Zurich, Switzerland

[73] Assignee: Biogen N.V., Curacao, Netherlands Antilles

[21] Appl. No.: 118,084

[22] Filed: Feb. 4, 1980

[30] Foreign Application Priority Data

Jan. 8, 1980 [EP] European Pat. Off. ....... 80.300079.3

[51] Int. Cl.³ .................... C12P 21/02; C12P 21/00; C12P 19/34; C12N 15/00; C12R 1/19; C07H 21/04; C12N 5/00; C12N 5/02; C12N 1/20; C12N 1/00

[52] U.S. Cl. ....................................... 435/70; 435/68; 435/91; 435/172.3; 435/240; 435/241; 435/253; 435/317; 435/317; 435/84; 435/849; 536/27; 935/11; 935/18; 935/29; 935/60; 935/72; 935/73; 935/67; 935/68; 935/69; 935/72; 424/85

[58] Field of Search .................. 435/811, 68, 70, 172, 435/253, 317, 91, 172.3; 536/27; 424/85

[56] References Cited

U.S. PATENT DOCUMENTS

| | | | |
|---|---|---|---|
| 3,699,222 | 10/1972 | Isaacs et al. | 424/85 |
| 4,184,917 | 1/1980 | Dorner et al. | 435/68 |
| 4,190,495 | 2/1980 | Curtiss | 435/172 |
| 4,237,224 | 12/1980 | Cohen et al. | 435/68 |
| 4,241,174 | 12/1980 | Familletti | 435/811 X |
| 4,262,090 | 4/1981 | Colby | 435/811 X |

FOREIGN PATENT DOCUMENTS

| | | |
|---|---|---|
| 0011560 | 5/1980 | European Pat. Off. . |
| 0018218 | 10/1980 | European Pat. Off. . |
| 0020147 | 12/1980 | European Pat. Off. . |
| 2724918 | 12/1978 | Fed. Rep. of Germany . |
| 2930604 | 2/1980 | Fed. Rep. of Germany . |
| 1412591 | 11/1975 | United Kingdom . |
| 1568047 | 5/1978 | United Kingdom . |
| 1521032 | 8/1978 | United Kingdom . |
| 2019408 | 10/1979 | United Kingdom . |
| 2027033 | 2/1980 | United Kingdom . |
| 2031434 | 4/1980 | United Kingdom . |
| 2033905 | 5/1980 | United Kingdom . |
| 2034323 | 6/1980 | United Kingdom . |
| 2034717 | 6/1980 | United Kingdom . |
| 2037296 | 7/1980 | United Kingdom . |

OTHER PUBLICATIONS

Goeddel et al.: Nature 290, 20 (1981).
Nature 286, 110 (1980).
Weissmann: in *Interferon* 1981, vol. 3, Gresser (ed.), Academic Press, New York, 1981, pp. 101–134.
Kennell, Progr. Nucl. Acid Res. Mol. Biol. 11, 259 (1971).
Britten et al., Quarterly Rev. Biol. 446, 111 (1971).
Berg et al., Conference on Regulatory Functions of Interferons, Abstract #19 (1979).
Rougeon et al., Nucl. Acids Res. 2, 2365 (1975).
Goeddel et al., "The Structure of Eight Distinct Cloned Human Leukocyte Interferon cDNAs", Nature, vol. 290, pp. 20–26 (1981).
Abstracts, "Conference on Regulatory Functions of Interferons", New York Academy of Sciences (Oct. 23–26, 1979).
"Purification of Interferon mRNA by Hybridizing Induced Material to cDNA", *Research Disclosure*, No. 18309, pp. 361–62 (Jul. 1979).
R. Ambler et al., "Partial Amino Acid Sequence of Penicillinase Coded by Escherichia Coli Plasmid R6K", *Proc. Natl. Acad. Sci USA*, 75, pp. 3752–36 (Aug. 1978).
P. Beverley et al., "Killing Comes Naturally", *Nature*, 278, pp. 119–20 (Mar. 8, 1979).
F. Bolivar et al., "Construction and Characterization of New Cloning Vehicles II, A Multipurpose Cloning System", *Gene*, 2, pp. 95–113 (1977).
P. Bridgen et al., "Human Lymphoblastoid Interferon", *J. Biol. Chem.*, 252, pp. 6585–87 (1977).
S. Broome et al., "Immunological Screening Method to Detect Specific Translation Products", *Proc. Natl. Acad. Sci. USA*, 75, pp. 2746–49 (Jun. 1978).
C. Burrell et al., "Expression in Escherichia coli of Hepatitis B Virus DNA Sequences Cloned in Plasmid pBR322", *Nature*, 279, pp. 43–47 (May 3, 1979).
M. Casdaban et al., "Lactose Genes Fused to Exogenous Promoters in One Step Using a Mu-Lac Bacteriophage: In Vivo Probe for Transcriptional Control Sequences", *Proc. Natl. Acad. Sci. USA,* 76, pp. 4530-33 (Sep. 1979).

R. Cavalieri et al., "Synthesis of Human Interferon By Xenopus Laevis Oocytes: Two Structural Genes For Interferons in Human Cells", *Proc. Natl. Acad. Sci. USA,* 74, pp. 3287-91 (Aug. 1977).

A. C. Y. Chang et al., "Phenotypic Expression in *E. coli* Of A DNA Sequence Coding For Mouse Dihydrofolate Reductase", *Nature,* 275, pp. 617-24 (Oct. 19, 1978).

P. Farrell et al., "Interferon Action: Two Distinct Pathways For Inhibition of Protein Synthesis By Double-Stranded RNA", *Proc. Natl. Acad. Sci. USA,* 75, pp. 5893-97, (Dec. 1978).

T. H. Fraser et al., "Chicken Ovalbumin Is Synthesized and Secreted By *Escherichia coli*", *Proc. Natl. Acad. Sci. USA,* 75, pp. 5936-40 (Dec. 1978).

A. Fritsch et al., "Clonage du Génome du Virus de l'Hepatite B Dans *Escherichia coli*", *C. R. Acad. Sc. Paris,* 287, Série D, pp. 1453-56 (Dec. 18, 1978).

J. Fujisawa et al., "Nonglycosylated Mouse L Cell Interferon Produced by the Action of Tunicamycin", *J. Biol. Chem.,* 253, pp. 8677-79 (1978).

D. Goeddel et al., "Direct Expression in *Escherichia Coli* Of A DNA Sequence Coding For Human Growth Hormone", *Nature,* 281, pp. 544-48 (Oct. 18, 1979).

D. Goeddel et al., "Expression in Escherichia coli of Chemically Synthesized Genes for Human Insulin", *Proc. Natl. Acad. Sci. USA,* 76, pp. 106-10 (Jan. 1979).

M. Grunstein et al., "Colony Hybridization: A Method for the Isolation of Cloned DNAs That Contain A Specific Gene", *Proc. Natl. Acad. Sci. USA,* 72, pp. 3961-65 (Oct. 1975).

E. Havell et al., "Altered Molecular Species of Human Interferon Produced In The Presence of Inhibitors of Glycosylation", *J. Biol. Chem.,* 252, pp. 4425-27 (1977).

R. Herberman et al., "Augmentation By Interferon Of Human Natural And Antibody-Dependent Cell-Mediated Cytotoxicity", *Nature,* 277, pp. 221-23 (Jan. 18, 1979).

K. Itakura et al., "Expression In Escherichia Coli Of A Chemically Synthesized Gene For The Hormone Somatostatin", *Science,* 198, pp. 1056-63 (Dec. 9, 1977).

I. Kerr et al., "pppA2'p5'A2'p5'A: An Inhibitor Of Protein Synthesis Synthesized With An Enzyme Fraction From Interferon-Treated Cells", *Proc. Natl. Acad. Sci. USA,* 75, pp. 256-60 (Jan. 1978).

E. Knight, Jr., "Interferon: Purification and Initial Characterization from Human Diploid Cells", *Proc. Natl. Acad. Sci. USA,* 73, pp. 520-23 (Feb. 1976).

J. Lewis et al., "Dual Action Of Double-Stranded RNA In Inhibiting Protein Synthesis In Extracts Of Interferon-Treated Mouse L Cells", *Eur. J. Biochem.,* 86, pp. 497-509 (1978).

J. Martial et al., "Human Growth Hormones: Complementary DNA Cloning And Expression In Bacteria", *Science,* 205, pp. 602-06 (Aug. 10, 1979).

A. Maxam et al., "A New Method For Sequencing DNA", *Proc. Natl. Acad. Sci. USA,* 74, pp. 560-64 (Feb. 1977).

O. Mercereau-Puijalon et al., "Synthesis Of An Ovalbumin-Like Protein By Escherichia coli K12 Harbouring A Recombinant Plasmid", *Nature,* 275, pp. 505-10 (Oct. 12, 1978).

S. Nagata et al., "Synthesis in E. coli Of A Polypeptide With Human Leukocyte Interferon Activity", *Nature,* 284, pp. 316-20 (Mar. 27, 1980).

A. Rosenfeld, "Interferon: The Next Wonder Therapy?", *The Reader's Digest,* pp. 130-33 (Nov. 1979).

M. Rubinstein et al., "Human Leukocyte Interferon Purified To Homogeneity", *Science,* 202, pp. 1289-90 (Dec. 22, 1978).

M. Rubinstein et al., "Human Leukocyte Interferon: Production, Purification to Homogeneity, And Initial Characterization", *Proc. Natl. Acad. Sci. USA,* 76, pp. 640-44 (Feb. 1979).

P. H. Seeburg et al., "Synthesis Of Growth Hormone by Bacteria", *Nature,* 276, pp. 795-98 (Dec. 21/28, 1978).

J. Shine et al., "Construction And Analysis Of Recombinant DNA For Human Chorionic Somatomammotropin", *Nature,* 270, pp. 494-99 (Dec. 8, 1977).

J. Sutcliffe, "Nucleotide Sequence Of The Ampicillin Resistance Gene of *Escherichia Coli* Plasmid pBR322", *Proc. Natl. Acad. Sci USA,* 75, pp. 3737-41 (Aug. 1978).

T. Taniguchi et al., "Construction And Identification Of A Bacterial Plasmid Containing The Human Fibroblast Interferon Gene Sequence", *Proc. Japan. Acad.,* 55, Ser. B., pp. 464-69 (1979).

J. Treuner et al., "Successful Treatment Of Nasopharyngeal Carcinoma With Interferon", preprint.

L. Villa-Komaroff et al., "A Bacterial Clone Synthesizing Proinsulin", *Proc. Natl. Acad. Sci. USA*, 75, pp. 3727-31 (Aug. 1978).

R. Wagner, "Biological Studies Of Interferon I. Supression Of Cellular Infection With Eastern Equine Encephalomyelitis Virus", Virology, 13, pp. 323-37 (1961).

K. Zoon, "Amino Terminal Sequence Of The Major Component of Human Lymphoblastoid Interferon", *Science*, 207, pp. 527-28 (Feb. 1, 1980).

*Primary Examiner*—Thomas G. Wiseman
*Assistant Examiner*—James Martinell
*Attorney, Agent, or Firm*—James F. Haley, Jr.

[57] ABSTRACT

Recombinant DNA molecules and hosts transformed with them which produce polypeptides displaying a biological or immunological activity of human interferon, the gene coding for these polypeptides and methods of making and using these molecules, hosts, genes and polypeptides. The recombinant DNA molecules are characterized by structural genes that code for a polypeptide displaying a biological or immulogical activity of human interferon. In appropriate hosts these molecules permit the production and identification of genes and polypeptides displaying a biological or immunological activity of human interferon and their use in antiviral and antitumor or anticancer agents.

18 Claims, 7 Drawing Figures

```
                    10                                    20
         MetSerIleGlnHisPheArgValAlaAlaLeuIleProPhePheAlaAlaPheCysLeuProValPheAlaHisProGluThr
pBR322   ATGAGTATTCAACATTTCCGTGTCGCCCTTATTCCCTTTTTTGCGGCATTTTGCCTTCCTGTTTTTGCTCACCCAGAAACG
         29      181
         LeuVal  ProAlaAlaMet
         CTGGTG...CCTGCAGCAATG...
                   ‾‾‾‾‾‾
                    Pst

24
         MetSerIleGlnHisPheArgValAlaAlaLeuIleProPhePheAlaAlaPheCysLeuProValPheAlaHisProArgCysSerAsn
pKT279   ATGAGTATTCAACATTTCCGTGTCGCCCTTATTCCCTTTTTTGCGGCATTTTGCCTTCCTGTTTTTGCTCACCGCTGCAGCAATG...
                                                                                   ‾‾‾‾‾‾
                                                                                    Pst

25
         MetSerIleGlnHisPheArgValAlaAlaLeuIleProPhePheAlaAlaPheCysLeuProValPheAlaHisProArgCysProLeuGlnGln
pKT280   ATGAGTATTCAACATTTCCGTGTCGCCCTTATTCCCTTTTTTGCGGCATTTTGCCTTCCTGTTTTTGCTCACCCGCTGCAGCAATG...
                                                                                    ‾‾‾‾‾‾
                                                                                     Pst

27
         MetSerIleGlnHisPheArgValAlaAlaLeuIleProPhePheAlaAlaPheCysLeuProValPheAlaHisProGluThr
pKT287   ATGAGTATTCAACATTTCCGTGTCGCCCTTATTCCCTTTTTTGCGGCATTTTGCCTTCCTGTTTTTGCTCACCCAGAAACG
         AlaAlaAlaMet
         GCTGCAGCAATG...
         ‾‾‾‾‾‾
          Pst
```

FIG 6

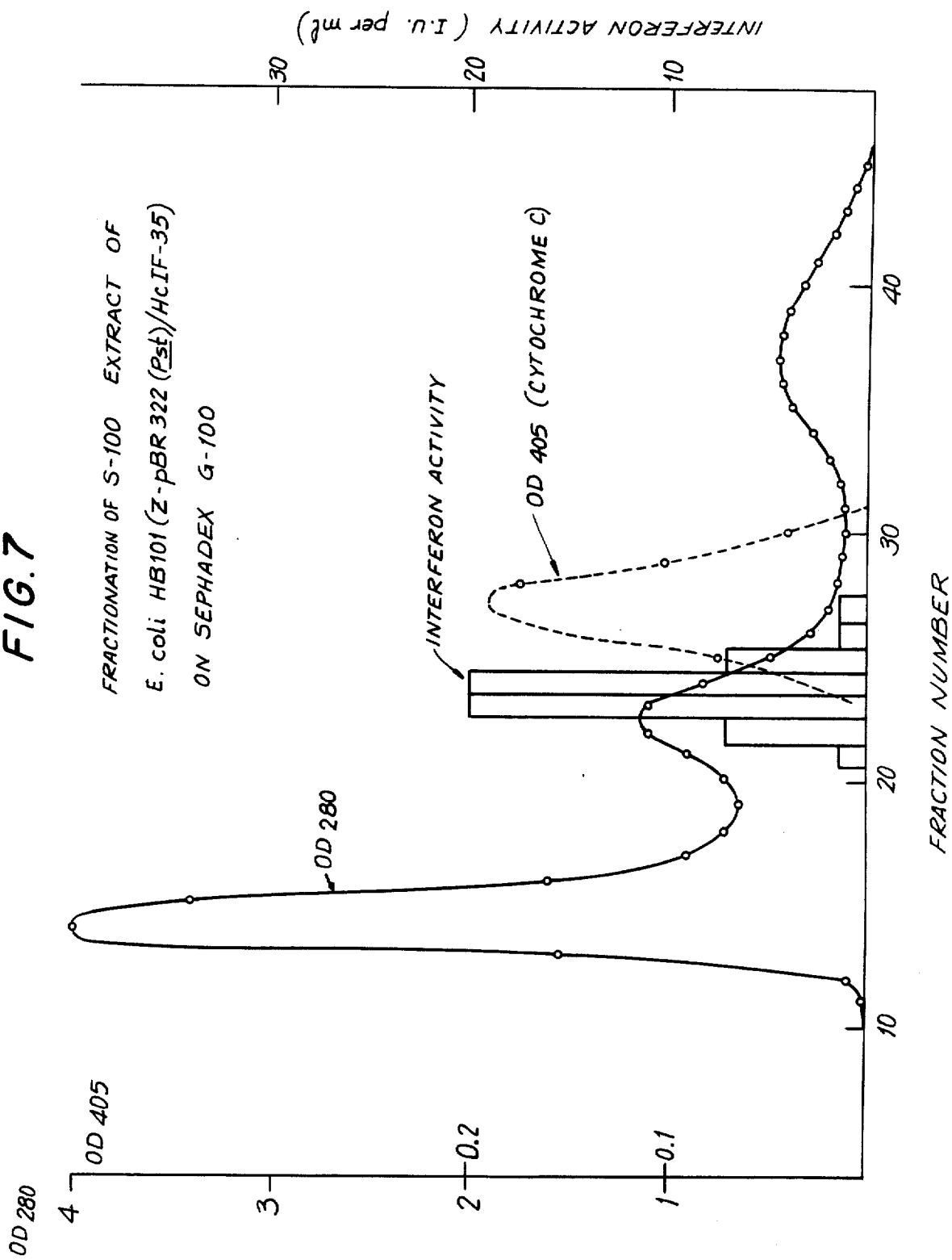

RECOMBINANT DNA MOLECULES AND THEIR USE IN PRODUCING HUMAN INTERFERON-LIKE POLYPEPTIDES

TECHNICAL FIELD OF INVENTION

This invention relates to recombinant DNA molecules and their use in producing interferon-like polypeptides. More particularly, the invention relates to recombinant DNA molecules expressed in appropriate host organisms. The recombinant DNA molecules disclosed herein are characterized by DNA that codes for polypeptides having an immunological or biological activity of human interferon. As will be appreciated from the disclosure to follow, the recombinant DNA molecules of this invention may be used in the production of polypeptides useful in antiviral and antitumor or anticancer agents.

BACKGROUND ART

In this application the interferon nomenclature announced in *Nature*, 286, p. 110 (July 10, 1980) is used. E.g., leukocyte interferon is designated IFN-α.

Two classes of interferons ("IF") are known to exist. Interferons of Class I are small, acid stable (glyco)-proteins that render cells resistant to viral infection (A. Isaacs and J. Lindenmann, "Virus Interference I. The Interferon", *Proc. Royal Soc. Ser. B.*, 147, pp. 258–67 (1957) and W. E. Stewart, II, *The Interferon System*, Springer-Verlag (1979) (hereinafter "The Interferon System")). Class II IFs are acid labile. At present, they are poorly characterized. Although to some extent cell specific (*The Interferon System*, pp. 135–45), IFs are not virus specific. Instead, IFs protect cells against a wide spectrum of viruses.

Two antigenically distinct species of Class I human interferon ("HIF") are known to exhibit IF activity. One IF species (F) is produced in diploid fibroblast cells. Another IF species (Le) is produced together with minor amounts of F IF in human leukocyte and lymphoblastoid cells. Both are heterogeneous in regard to size, presumably because of the carbohydrate moiety. F IF has been extensively purified and characterized (E. Knight, Jr., "Interferon: Purification And Initial Characterization From Human Diploid Cells", *Proc. Natl. Acad. Sci. USA*, 73, pp. 520–23 (1976)). It is a glycoprotein of 20,000–26,500 molecular weight (J. Wassenbach et al., "Identification Of The Translation Products Of Human Fibroblast Interferon mRNA In Reticulocyte Lysates", *Eur. J. Biochem.* 98, pp. 1–8 (1979)). Elucidation of its amino acid sequence is in progress. Two distinct genes, one located on chromosome 2, the other on chromosome 5, code for F IF (D. L. Slate and F. H. Ruddle, "Fibroblast Interferon In Man Is Coded By Two Loci On Separate Chromosomes", *Cell*, 16, pp. 171–80 (1979)). Le IF has likewise been purified and characterized. Two components have been described, one of 21000 to 22000 and the other of 15000 to 18000 molecular weight. The component of lower molecular weight appears to represent the non-glycosylated form (W. E. Stewart, II et al., "Effect of Glycosylation Inhibitors On The Production And Properties Of Human Leukocyte Interferon", *Virology*, 97, pp. 473–76 (1979); M. Rubinstein et al., "Human Leukocyte Interferon: Production, Purification To Homogeneity And Initial Characterization", *Proc. Natl. Acad. Sci. USA*, 76, pp. 640–44 (1979); M. Rubenstein et al., "Human Leukocyte Interferon Purified to Homogeneity", *Science*, 202, pp. 1289–90 (1978); P. J. Bridgen et al., "Human Lymphoblastoid Interferon", *J. Biol. CHem.*, 252, pp. 6585–87 (1977); K. C. Zoon et al., "Purification And Partial Characterization Of Human Lymphoblastoid Interferon", *Proc. Natl. Acad. Sci. USA*, 76, pp. 5601–05 (1979); and *The Interferon System*, p. 173 and references cited therein). A portion of the amino acid sequence of Le IF has been determined, i.e., 20 amino acids from the amino terminus of the polypeptide.

The two species of HIF have a number of different properties. For example, anti-human Le IF antibodies are less efficient against F IF and anti-sera to human F IF have no activity against human Le IF (*The Interferon System*, p. 151) and Le IF displays a high degree of activity in cell cultures of bovine, feline or porcine origin whereas F IF is hardly active in those cells. In addition, the two IFs result from different mRNA species (and therefore presumable different structural genes) that code for polypeptides of different primary sequence (R. L. Cavalieri et al., "Synthesis Of Human Interferon By *Xenopus laevis* Oocytes: Two Structural Genes For Interferon In Human Cells", *Proc. Natl. Acad. Sci. USA*, 74, pp. 3287–91 (1977)).

Although both Le and F IFs occur in a glycosylated form, removal of the carbohydrate moiety (P. J. Bridgen et al., supra) or synthesis of IF in the presence of inhibitors which preclude glycosylation (W. E. Stewart, II et al., *Virology*, supra; J. Fujisawa et al., "Nonglycosylated Mouse L Cell Interferon Produced By The Action Of Tunicamycin", *J. Biol. Chem.*, 253, pp. 8677–79 (1978)) yields a smaller form of IF which still retains most or all of its IF activity.

Both F IF and Le IF may, like many human proteins, be polymorphic. Therefore, cells of particular individuals may produce IF species within each of the more general F IF and Le IF classes which are physiologically similar but structurally slightly different than the class of which it is a part. Therefore, while the protein structure of the F IF or Le IF may be generally well-defined, particular individuals may produce IFs that are slight variations thereof.

IF is usually not detectable in normal or healthy cells (*The Interferon System*, pp. 55–57). Instead, the protein is produced as a result of the cell's exposure to an IF inducer. IF inducers are usually viruses but may also be non-viral in character, such as natural or synthetic double-stranded RNA, intracellular microbes, microbial products and various chemical agents. Numerous attempts have been made to take advantage of these non-viral inducers to render human cells resistant to viral infection (S. Baron and F. Dianzani (eds.), *Texas Reports On Biology And Medicine*, 35 ("Texas Reports"), pp. 528–40 (1977)). These attempts have not been very successful. Instead, use of exogenous IF itself is now preferred.

As an antiviral agent, HIF has been used to treat the following: respiratory infections, (*Texas Reports*, pp. 486–96); herpes simplex keratitis (*Texas Reports*, pp. 497–500); acute hemorrhagic conjunctivitis, (*Texas Reports*, pp. 501–10); varicella zoster, (*Texas Reports*, pp. 511–15); cytomegalovirus infection (*Texas Reports*, pp. 523–27); and hepatitis B, (*Texas Reports*, pp. 516–22). See also *The Interferon System*, pp. 307–19. However, large scale use of IF as an antiviral agent requires larger amounts of HIF than heretofore have been available.

IF has other effects in addition to its antiviral action. For example, it antagonizes the effect of colony stimulating factor, inhibits the growth of hemopoietic colony-forming cells and interferes with the normal differentiation of granulocyte and macrophage precursors (*Texas Reports*, pp. 343-49). It also inhibits erythroid differentiation in DMSO-treated Friend leukemia cells (*Texas Reports*, pp. 420-28). IF may also play a role in regulation of the immune response. Depending upon the dose and time of application in relation to antigen, Le IF can be both immunopotentiating and immunosuppressive in vivo and in vitro (*Texas Reports*, pp. 357-69). In addition, specifically sensitized lymphocytes have been observed to produce IF after contact with antigen. Such antigen-induced IF could therefore be a regulator of the immune response, affecting both circulating antigen levels and expression of cellular immunity (*Texas Reports*, pp. 370-74). IF is also known to enhance the activity of killer lymphocytes and antibody-dependent cell-mediated cytotoxicity (R. R. Herberman et al., "Augmentation By Interferon Of Human Natural And Antibody Dependent Cell-Mediated Cytotoxicity", *Nature*, 277, pp. 221-23 (1979); P. Beverley and D. Knight, "Killing Comes Naturally", *Nature*, 278, pp. 119-20 (1979); *Texas Reports*, pp. 375-80). Both of these species are probably involved in the immunological attack on tumor cells.

Therefore, in addition to its use as a human antiviral agent, HIF has potential application in antitumor and anticancer therapy (*The Interferon System*, pp. 319-21). It is now known that IFs affect the growth of many classes of tumors in many animals (*The Interferon System*, pp. 292-304). They, like other antitumor agents, seem most effective when directed against small tumors. The antitumor effects of animal IF are dependent on dosage and time but have been demonstrated at concentrations below toxic levels. Accordingly, numerous investigations and clinical trials have been and continue to be conducted into the antitumor and anticancer properties of HIFs. These include treatment of several malignant diseases such as osteosarcoma, acute myeloid leukemia, multiple myeloma and Hodgkin's disease (*Texas Reports*, pp. 429-35). Although the results of these clinical tests are encouraging, the antitumor and anticancer applications of HIF have been severely hampered by lack of an adequate supply of purified HIF.

At the biochemical level IFs induce the formation of at least 3 proteins, a protein kinase (B. Lebleu et al., "Interferon, Double-Stranded RNA And Protein Phosphorylation", *Proc. Natl. Acad. Sci. USA*, 73, pp. 3107-11 (1976), A. G. Hovanessian and I. M. Kerr, "The (2'-5') Oligoadenylate (ppp A2'-5'A2'-5'A) Synthetase And Protein Kinase(s) From Interferon-Treated Cells", *Eur. J. Biochem.*, 93, pp. 515-26 (1979)), a (2'-5')oligo(A) polymerase (A. G. Hovanessian et al., "Synthesis Of Low-Molecular Weight Inhibitor Of Protein Synthesis With Enzyme From Interferon-Treated Cells", *Nature*, 268, pp. 537-39 (1977), A. G. Hovanessian and I. M. Kerr, *Eur. J. Biochem.*, supra) and a phosphodiesterase (A. Schmidt et al., "An Interferon-Induced Phosphodiesterase Degrading (2'-5')oligoisoadenylate And The C-C-A Terminus of tRNA", *Proc. Natl. Acad. Sci. USA*, 76, pp. 4788-92 (1979)). The appearance of these enzymes in cells treated with IF should allow a further characterization of proteins with IF-like activity.

Today, human leukocyte IF is produced either through human cells grown in tissue culture or through human leukocytes collected from blood donors. $2.6 \times 10^9$ IU of crude IF have been reported from 800 l of cultured Namalva cells (P. J. Bridgen et al., supra). At very large blood centers, e.g., the Finnish Red Cross Center in Helsinki, Finland, the production capacity is about $10^{11}$ IU annually. Since dosage is typically $3 \times 10^6$ IU per patient per day, neither of these sources are adequate to provide the needed commercial quantities of HIF. Therefore, production of IF by other procedures is attractive.

The crude IF produced as above may be purified to higher specific activity. For example, in yields of about 25%, Le IF isolated from blood cells has been purified to about $10^9$ IU/mg (L. S. Lin et al., "Purification Of Human Leukocyte Interferon To Apparent Homogeneity: Criteria For Purity", *Abs. Ann. Meeting Amer. Soc. Microbiol.* (1978) and *The Interferon System*, pp. 156-71). Because the specific activity of IF is so high, in the order of $4.0 \times 10^8-10^9$ IU/mg, the amount of IF protein required for commercial applications is low. For example, 100 grams of pure IF would provide between 3 and 30 million doses.

Recent advances in molecular biology have made it possible to introduce the DNA coding for specific non-bacterial eukaryotic proteins into bacterial cells. In general, with DNA other than that prepared via chemical synthesis, the construction of such recombinant DNA molecules comprises the steps of producing a single-stranded DNA copy (cDNA) of a purified messenger RNA (mRNA) template for the desired protein; converting the cDNA to double-stranded DNA; linking the DNA to an appropriate site in an appropriate cloning vehicle to form a recombinant DNA molecule and transforming an appropriate host with that recombinant DNA molecule. Such transformation may permit the host to produce the desired protein.

Several non-bacterial proteins and genes have been obtained in *E. coli* using recombinant DNA technology. These include a protein displaying rat proinsulin antigenic determinants (L. Villa-Komaroff et. al., "A Bacterial Clone Synthesizing Proinsulin", *Proc. Natl. Acad. Sci. USA*, 75, pp. 3727-31 (1978)), rat growth hormone (P. H. Seeburg et al., "Synthesis Of Growth Hormone By Bacteria", *Nature*, 276, pp. 795-98 (1978)), mouse dihydrofolate reductase (A. C. Y. Chang et al., "Phenotypic Expression in *E. coli* Of A DNA Sequence Coding For Mouse Dihydrofolate Reductase", *Nature*, 275, pp. 617-24 (1978)), human somatostatin (K. Itakura et al., "Expression in *Escherichia coli* Of A Chemically Synthesized Gene For The Hormone Somatostatin", *Science*, 198, pp. 1056-63 (1977)); European patent applications 0,001,929, 0,001,930, and 0,001,931 and cognate applications in other countries), the A and B polypeptide chains of human insulin (D. V. Goeddel et al., "Expression in *Escherichia coli* Of Chemically Synthesized Genes For Human Insulin", *Proc. Natl. Acad. Sci. USA*, 76, pp. 106-10 (1979) and the European and related patent specifications, supra), antigens of human hepatitis B virus (C. J. Burrell et al., "Expression in *Escherichia coli:* Of Hepatitis B Virus DNA Sequences Cloned In Plasmid pBR322", *Nature*, 279, pp. 43-7 (1979) and M. Pasek et al., "Hepatitis B Virus Genes And Their Expression In *E. coli*", *Nature*, 282, pp. 575-79 (1979)), human growth hormone (D. V. Goeddel et al., "Direct Expression In *Escherichia coli* Of A DNA Sequence Coding For Human Growth Hormone", *Nature*, 281, pp. 544-51 (1979)), and SV40 t antigen (T. M. Roberts et al., "Synthesis Of Simian Virus 40 t Antigen In *Escherichia coli*", *Proc. Natl. Acad. Sci. USA*, 76, pp. 5596-600 (1979)).

In addition, at least in the case of ovalbumin DNA, it is known that appropriate fusion of the particular DNA to a strong bacterial promoter or expression control sequence produces larger amounts of the desired ovalbumin-like protein, i.e., about 0.5 to 1% of the total protein mass of an *E. coli* cell (O. Mercereau-Puijalon et al., "Synthesis Of An Ovalbumin-Like Protein By *Escherichia coli* K12 Harboring A Recombinant Plasmid", *Nature*, 275, pp. 505-10 (1978); T. H. Fraser and B. J. Bruce, "Chicken Ovalbumin Is Synthesized And Secreted By *Escherichia coli*", *Proc. Natl. Acad. Sci. USA*, 75, pp. 5936-40 (1978)).

None of the foregoing, however is directed, as is this invention, toward the synthesis of HIF with use of recombinant DNA technology. Moreover, the execution of each of the foregoing examples is enhanced by the availability of the sequence information required to prepare a synthetic gene (Itakura et al., supra) or of a cell type or virus rich in a particular DNA sequence (C. J. Burrell et al., supra) or mRNA species (Villa-Komaroff et al., supra) which readily allows preparation and identification of bacterial clones containing the desired hybrid DNA, or of a system allowing the selection of *E. coli* expressing the desired protein (A.C.Y. Chang et al., supra). No such facilitating circumstances exist in the case of the IF system.

DISCLOSURE OF THE INVENTION

The present invention solves the problems referred to by providing at least one recombinant DNA molecule characterized by a structural gene coding for a polypeptide displaying an immunological or biological activity of HIF.

By virtue of this invention, it is possible to obtain polypeptide(s) displaying an immunological or biological activity of HIF for use as antiviral, antitumor or anticancer agents. The methods of this invention should allow the production of these polypeptides in amounts and by methods hitherto not available.

As will be appreciated from the disclosure to follow, the recombinant DNA molecules of the invention are capable of directing the production, in an appropriate host, of a polypeptide displaying an immunological or biological activity of HIF. Replication of these recombinant DNA molecules in an appropriate host also permits the production in large quantities of genes coding for these polypeptides. The molecular structure and properties of these polypeptides and genes may be readily determined. The polypeptides and genes are useful, either as produced in the host or after appropriate derivatization or modification, in compositions and methods for detecting and improving the production of these products themselves and for use in antiviral and antitumor or anticancer agents.

This process may be distinguished from the prior processes, above mentioned, in that none of the prior processes involved the preparation of recombinant DNA molecules which contained gene inserts coding for a polypeptide displaying an immunological or biological activity of HIF, and none involved the screening problems associated with this preparation.

BRIEF DESCRIPTION OF THE DRAWINGS

FIG. 6 displays the partial nucleotide sequence of some cloning vehicles useful in accordance with this invention.

FIG. 7 displays the results of a Sephadex G-100 fractionation of supernatant prepared from a bacterial culture of this invention.

BEST MODE OF CARRYING OUT THE INVENTION

Figure 1:
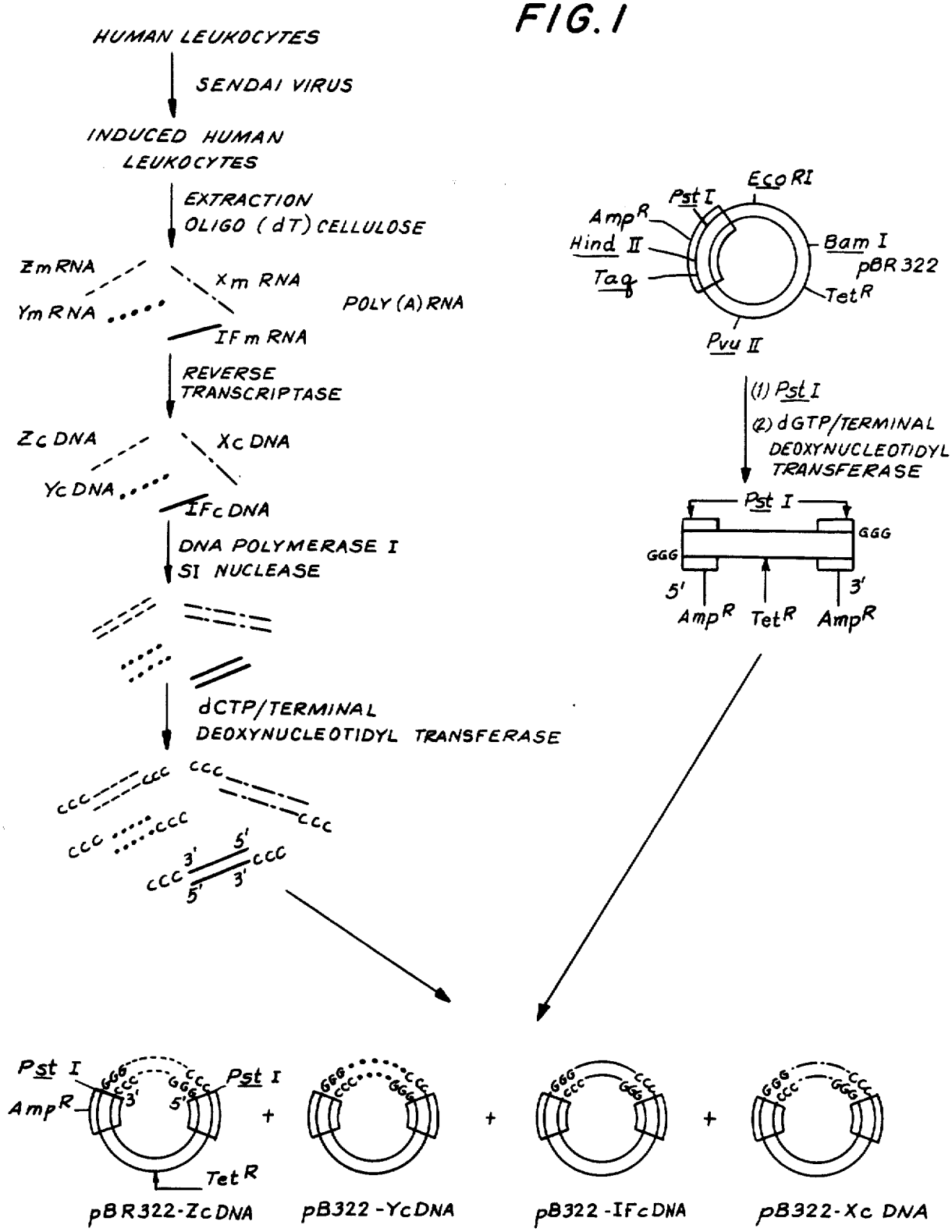
FIG. 1 is a schematic outline of one embodiment of a process of this invention for preparing a mixture of recombinant DNA molecules, some of which are characterized by inserted DNA sequences that code for polypeptides of this invention.

In order that the invention herein described may be more fully understood, the following detailed description is set forth.

In the description the following terms are employed:

Neucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is nucleoside. The base characterizes the nucleotide. The four DNA bases are adenine ("A"), guanine ("G"), cytosine ("C") and thymine ("T"). The four RNA bases are A, G, C and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode for the amino acid leucine ("Leu"), TAG, TAA and TGA are translation stop signals and ATG is a translation start signal.

Reading Frame—The grouping of codons during translation of mRNA into amino acid sequences. During translation the proper reading frame must be maintained. For example, the sequence GCTGGTTGTAAG may be translated in three reading frames or phases, each of which affords a different amino acid sequence:

GCT GGT TGT AAG—Ala-Gly-Cys-Lys
G CTG GTT GTA AG—Leu-Val-Val
GC TGG TTG TAA G—Trp-Leu-(STOP)

Polypeptide—A linear array of amino acids connected one to the other by peptide bonds between the α-amino and carboxy groups of adjacent amino acids.

Genome—The entire DNA of a cell or a virus. It includes inter alia the structural genes coding for the polypeptides of the substance, as well as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A non-chromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance ($Tet^R$) transforms a cell previously sensitive to tetracycline into one which is resistant to it. A cell transformed by a plasmid is called a "transformant".

Phage or Bacteriophage—Bacterial virus many of which consist of DNA sequences encapsidated in a protein envelope or coat ("capsid").

Cloning Vehicle—A plasmid, phage DNA or other DNA sequences which are able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and have the capacity to infect some host cell and be maintained therein.

Expression Control Sequence—A sequence of nucleotides that controls and regulates expression of structural genes when operatively linked to those genes.

Referring now to FIG. 1, we have shown therein a schematic outline of one embodiment of a process for preparing a mixture of recombinant DNA molecules, some of which are characterized by inserted DNA sequences that code for polypeptides having an immunological or biological activity of human interferon.

PREPARATION OF POLY(A) RNA CONTAINING HUMAN INTERFERON mRNA (IFmRNA)

Human leukocytes were induced for 5 hours at 37° C. with Sendai virus and extracted to yield a poly(A) RNA mixture containing human interferon mRNA ("IFmRNA"). Induction was by the Cantell procedure (*The Interferon System*, pp. 130–31 and the references cited therein). The poly(A) RNA mixture is illustrated without regard to its actual proportions in FIG. 1. Induced leukocytes were harvested and $10^{11}$ cells were resuspended in 1 l of a solution containing 8 g NaCl, 0.2 g KCl, 1.15 g $Na_2HPO_4.2H_2O$ and $0.2KH_2PO_4$ dissolved in 1 l of water ("PBS") and added slowly with vigorous stirring to 17 l 20 mM Tris-HCl (pH 7.5), 1 mM EDTA ("TE buffer"), 2% sodium dodecyl sulfate ("SDS") in a 50 l separatory funnel. Self-digested Pronase (Calbiochem) was added to 200 µg/ml and the solution stirred for 1 h at room temperature. $10^6$ counts/minute ("cpm") of $^{125}I$-globin mRNA were added as a marker for recovery of the poly(A) RNA and to control for mRNA degradation during subsequent steps. 2M Tris-HCl (pH 9) in an amount equal to 1/20 of the total volume ("1/20 vol") was added and the mixture extracted with vigorous stirring with 15 l of redistilled phenol for 10 min. Three l chloroform were added and the mixture stirred for 5 min. After allowing 30 min for phase separation, the aqueous phase was removed and extracted again with phenol and chloroform. The resultant aqueous phase, totalling 19.1 l, was combined with 60 g SDS. Nucleic acids were precipitated from the aqueous phase with 1/10 vol 3M sodium acetate (pH 5.5) and 2 vol ethanol.

After storage overnight at −20° C., the fibrous nucleic acid precipitate was removed by filtration through a plastic tea sieve. This material was then stirred with 200 ml TNE (50 mM Tris-HCl (pH 7.5), 100 mM NaCl, 5 mM EDTA) containing 0.5% SDS. It subsequently dissolved on addition of a further 350 ml of that solution. The non-fibrous precipitate was collected by centrifugation in 1 l Sorvall bottles in a Sorvall RC-3 centrifuge for 15 min at 5,000 rpm and dissolved in 350 ml TNE containing 0.5% SDS. The two TNE solutions were combined, extracted 3 times with 1 vol phenol, 3 times with ½ vol ether and 3 times with 1 vol ether. RNA recovery from the aqueous phase totalled 775 mg, as measured by absorbance at 260 nm.

Isolation of the poly(A) RNA mixture was achieved by repeated batch adsorption to oligo(dT) cellulose (type 7, P-L Biochemicals, Inc.). 2.7 grams oligo(dT) cellulose were added to 500 ml, i.e., about half of the RNA-containing solution described above. After stirring for 1 h at room temperature to effect adsorption of the poly(A) RNA to the oligo(dT) cellulose, the cellulose and the mixture of mRNAs bound to it were collected by centrifugation and washed once with 50 ml TNE and a second time with 15 ml TNE. The bound poly(A) RNA was then eluted by five successive washes with 2 ml $H_2O$. The yield was 860 µg poly(A) RNA as measured by optical density (Preparation A). The supernatant RNA solution from the first adsorption was subjected to two further adsorption cycles, exactly as described above. The second and third adsorptions yielded 600 µg and 170 µg RNA respectively and were combined (Preparation B).

RNA was assayed for IFmRNA by injection into *Xenopus Laevis* oocytes (*The Interferon System*, pp. 93–95): RNA was dissolved in 15 mM Tris-HCl (pH 7.5), 88 mM NaCl ("TNK buffer") to give a concentration of about 1 mg/ml. Fifty nl of this solution were injected into each of 50 oocytes. The oocytes were incubated overnight at room temperature in Barth medium (Gurdon, *J. Embryol and Exper. Morph.*, 20, pp. 401–414 (1968) and Barth, *J. Embryol and Exper. Morph.*, 7, pp. 210–222 (1959)). The incubated oocytes were then rinsed and homogenized with a Pasteur pipette in a 1.5 ml Eppendorf centrifuge tube in 0.5 ml 52 mM Tris glycine buffer (pH 8.9). The mixture was centrifuged for 2 min in an Eppendorf centrifuge and the supernatant was drawn off and frozen at −20° C. for assay. IF activity was determined by the plaque reduction assay described by H. Strander and K. Cantell, "Production of Interferon By Human Leukocytes In Vitro", *Ann. Med. exp. Fenn.*, 44, pp. 265–73 (1966). One unit IF reduces virus plaques by 50%. The potency of an IF preparation is expressed relative to the human reference IF 69/19 (International Symposium on Standardization of Interferon and Interferon Inducers, 1969). Alternatively, the assay was based on the reduction of cytopathic effect, essentially as described by W. E. Stewart, II and S. E. Sulkin, "Interferon Production In Hamsters Experimentally Infected with Rabies Virus", *Proc. Soc. Exp. Biol. Med.*, 123, pp. 650-3 (1966), except that human CCL-23 cells were used and that challenge was with Mengo virus. The oocyte extracts had 300 IU of IF activity per μg of RNA injected. In later assays incubation of injected oocytes was for 48 hrs and only the incubation medium was assayed because most of the interferon is excreted by the oocytes (A. Colman and J. Morser, "Export of Proteins From Oocytes Of *Xenopus laevis*", Cell, 17, pp. 517-26 (1979)). For further purification of the poly(A) RNA sufficient 0.5M ethylene diamine tetraacetic acid ("EDTA") was added to the poly(A) RNA Preparation A to bring the concentration to 5 mM EDTA. The resultant solution was extracted twice with an equal vol of TNE-saturated phenol and 5 times with an equal vol of ether. It was then passed through a 0.1-ml Chelex-100 Bio-Rad column, heated for 90 sec at 100° C. and layered onto a 13-ml 5-23% sucrose gradient containing 50 mM Tris-HCl (pH 7.5), 1 mM EDTA, 0.2M NaCl. 10,000 cpm of 5'-terminally $^{32}$P-labeled DNA fragments produced by simultaneous digestion of pBR322 with restriction enzymes HindIII and PstI (New England Biolabs), were added as size markers. Centrifugation was in an SW40 rotor at 10° C. and 35,000 rpm for 16 h. Fractions (0.6 ml) were collected with an ISCO gradient collector at 1 ml/min. The fractions were assayed for IFmRNA as described above and their position relative to the $^{32}$P-DNA markers was noted for future reference. In subsequent centrifugations, IFmRNA-containing fractions were identified relative to the markers. The fractions with IFmRNA activity contained 80 μg of poly(A) RNA. They were mixed with 2 vol TNE containing 0.5% SDS and 0.02% polyvinyl sulfate (in later preparations polyvinyl sulfate was omitted) and applied to a 50-μl oligo(dT) cellulose column. After washing the column as described above, 40 μg of the RNA mixture were eluted with 4 washes of 0.6 ml sterile distilled water. After ethanol precipitation, the RNA was dissolved to 1 mg/ml in 0.5 mM EDTA.

An assay for IFmRNA activity was carried out as described above on a portion of the poly(A) RNA precipitate. It had a specific activity of 3600 IU interferon/μg of RNA injected. Therefore, the sucrose gradient had enriched the poly(A) RNA about 10-fold in regard to IF mRNA. In a subsequent, similar preparation about a 40-fold enrichment was obtained. Preparation B was purified similarly and, since it had a similar specific activity as Preparation A, the two were pooled.

At this point it should be recognized that the poly(A) RNA product obtained from the sucrose gradient contains a very large number of different mRNA's. Except for the mRNA specific for IF, the other mRNAs are undesirable contaminants (FIG. 1). Unfortunately, these contaminant RNAs behave similarly to IFmRNA throughout the remainder of the cloning process of this invention. Therefore, their presence in the poly(A) RNA will result in the ultimate preparation of a large number of unwanted bacterial clones which contain genes that code for polypeptides other than IF. This contamination presents complex screening problems in the isolation of the desired IF hybrid clones. In the case of IF, the screening problem is further exacerbated by the lack of a sufficiently purified sample of IFmRNA or DNA or portion thereof to act as a screening probe for the identification of the desired clones. Therefore, the screening process for the IF clones is very time-consuming and difficult. Because only a very small percentage of IF clones themselves are expected to express IF in a biologically active or immunologically active form, the isolation of an active clone is a "needle in a haystack" screening process.

In remedy of this almost insurmountable screening problem, it is one attribute of this invention to use recombinant DNA technology to provide a purified sample of IFmRNA or cDNA or a portion thereof. This purified mRNA or cDNA may then be used to screen rapidly very large numbers of bacterial clones and thereby markedly increase the probability of isolating a clone which expresses IF in an active form.

SYNTHESIS OF cDNA MIXTURE CONTAINING INTERFERON cDNA

The poly(A) RNA enriched for IFmRNA (Preparation A+B) was used as a template to prepare single-stranded complementary DNA (cDNA) (Fig. 1) (Cf, A. Efstratiadis et al., "Full Length And Discrete Partial Reverse Transcripts Of Globin And Chorion mRNAs", *Cell*, 4, pp. 367-78 (1975) and references cited therein). The 800-μl reaction mixture contained 40 mM Tris-HCl (pH 7.5), 30 mM NaCl, 5 mM MgCl$_2$, 0.5 mM DTT (Cal-Biochem), 20 μg/ml oligo(dT) 12-18 (P&L Biochemicals), 5 mM dGTP (Schwarz), dCTP (Laevosan) and dTTP (Sigma), 5 mM $^{32}$P-dATP (NEN, specific activity 100,000 cpm/nmole), 60 μg/ml poly(A) RNA and 280 units avian myeloblastosis virus (AMV) reverse transcriptase (a gift from Life Sciences, Inc., St. Petersburg, Fla.). After incubation for 1 h at 37° C., 0.5M EDTA and 20% SDS (recrystallized) were added to 10 mM EDTA and 0.1% SDS. The mixture was extracted with 1 vol phenol (distilled). The phenol phase was washed with 200 μl 200 mM Tris-HCl (pH 7.5), 1 mM EDTA and 0.1% SDS, and the aqueous phases combined. These were extracted with an equal vol ether (Fluka, pro anal.) and chromatographed on a 5-ml Sephadex G-100 column in TNE. Fractions of 0.1 ml were collected at 0.3 ml/min. Fractions displaying radioactivity (as measured by Cerenkov radiation) were combined and 3M sodium acetate added to 0.3M. The nucleic acids were precipitated with 2.5 vol of ethanol. After storage overnight at −20° C., the samples were centrifuged and the supernatant discarded. The precipitate was dissolved in 180 μl distilled water and transferred to a siliconized Eppendorf tube. 20 μl 5M NaOH were added and the mixture kept at room temperature for 40 min. 20 μl of 5M sodium acetate, 100 μl distilled water and 500 μl ethanol were added. After cooling overnight at −20° C., the resulting precipitate was collected by centrifugation at a force equivalent to 10,000 times the force of gravity (10000 xg) for 20 min at 0° C. The yield of single-stranded cDNA was 10 μg.

Again, it is to be understood that the single-stranded cDNA product prepared above is in reality a complex mixture of a large number of different cDNAs transcribed from the corresponding mRNAs present in the poly(A) RNA mixture (FIG. 1). Only a very few of these cDNAs are interferon related, i.e., IFcDNAs. Another factor also acts to complicate the cDNA mixture—each mRNA species of the poly(A) RNA mixture is usually not transcribed completely. Instead, for each mRNA species the transcription process may stop before the end of the mRNA is reached. Therefore, a large variety of cDNA species may be produced from each mRNA species (not shown in FIG. 1). Each species will behave more or less similarly in the subsequent cloning process so that bacterial clones will be produced which contain recombinant DNA molecules having only a fragment of the gene for a particular protein. The presence of these fragment-containing clones even further complicates the final clone screening process.

The sizes of the various single-stranded cDNAs were determined by electrophoresis of a small aliquot on a alkaline 2% agarose gel using 30 mM NaOH, 2 mM EDTA as electrolyte (M. W. McDonell et al., "Analysis Of Restriction Fragments Of T7 DNA And Determination Of Molecular Weights By Electrophoresis In Neutral And Alkaline Gels", *J. Mol. Biol.*, 110, pp. 119–46 (1977)). The $^{32}$P-cDNA had a length of 600–1000 nucleotides, relative to single-stranded globin cDNA and $^{32}$P-labeled DNA fragments used as size markers.

PREPARATION OF DOUBLE-STRANDED cDNA

The single-stranded cDNA may be rendered double-stranded by treatment with DNA polymerase I (T. Maniatis et al., "Amplification And Characterization Of A $\beta$-Globin Gene Synthesized In Vitro", *Cell*, 8, pp. 163–82 (1976)). The precipitated single-stranded cDNA from above was dissolved in 200 $\mu$l H$_2$O, heated at 100° C. for 2 min and incubated in 500 $\mu$l 0.1M heat denatured potassium phosphate buffer (pH 6.9), 10 mM MgCl$_2$, 10 mM DTT (Calbiochem), 1 mM each of dATP (Merck), dGTP (Schwarz) and dCTP (Laevosan), 1 mM $^3$H-dTTP (NEN, specific activity 100,000 cpm/nmole) and 150 units/ml of *E. coli* DNA polymerase I (Boehringer-Mannheim). After 6.5 h at 15° C., 0.5M EDTA and 20% SDS were added to 10 mM EDTA and 0.1% SDS. The mixture was then extracted with 500 $\mu$l phenol and the phenol phase was reextracted with 250 $\mu$l 20 mM Tris-HCl (pH 7.5), 5 mM EDTA ("TE buffer"). The two aqueous phases were combined and chromatographed on a 5-ml Sephadex G-100 column under the same conditions described previously. Sodium acetate (3M) was added to 0.3M and 2.5 vol ethanol were mixed into precipitate the DNA. A total of 13 $\mu$g DNA was recovered.

The DNA was treated with nuclease S$_1$, prepared by the method of R. C. Weigand et al., "Specificity Of The S$_1$ Nuclease From *Aspergillus oryzae*", *j. Biol. Chem.*, 250, pp. 8848–55 (1975). The precipitated DNA was dissolved in 250 $\mu$l S$_1$ buffer (0.2M NaCl, 50 mM sodium acetate (pH 4.5), 10 mM zinc sulfate) and warmed at 37° C. for 30 min. 1.5 $\mu$l S$_1$ enzyme (11 units/$\mu$l) were added and the mixture incubated at 37° C. for 30 min. SDS and EDTA were added to 0.1% SDS and 5 mM EDTA, and the mixture was extracted with 250 $\mu$l phenol. The phenol phase was washed with 100 $\mu$l TE buffer. The aqueous phases were combined and chromatographed on a Sephadex G-100 (Pharmacia) column in TNE; 0.1-ml fractions were collected at 0.3 ml/min and the Cerenkov radiation of each fraction was determined. 8 $\mu$g of double-stranded cDNA were recovered after precipitation with ethanol and sodium acetate as above.

Again, it must be recognized that the double-stranded cDNA produced above is a mixture of a large number of cDNAs and fragments thereof, only a very few of which are IFcDNA or its fragments (FIG. 1).

CLONING OF DOUBLE-STRANDED DNA

A wide variety of host/cloning vehicle combinations may be employed in cloning the double-stranded cDNA prepared in accordance with this invention. For example, useful cloning vehicles may consist of segments of chromosomal, non-chromosomal and synthetic DNA sequences, such as various known bacterial plasmids, e.g., plasmids from *E. coli* including col E1, pCR1, pBR322 and their derivatives, wider host range plasmids, e.g., RP4, phage DNA, e.g., the numerous derivatives of phage $\lambda$ e.g., NM 989, and vectors derived from combinations of plasmids and phage DNAs such as plasmids which have been modified to employ phage DNA or other expression control sequences or yeast plasmids such as the 2 u plasmid or derivatives thereof. Useful hosts may include bacterial hosts such as *E. coli* HB 101, *E. coli* X1776, *E. coli* X2282, *E. coli* MRCI and strains of Pseudomonas, *Bacillus subtilis, Bacillus stearothermophilus* and other bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning vehicle, various sites may be selected for insertion of the double-stranded DNA. These sites are usually designated by the restriction endonuclease which cuts them. For example, in pBR322 the PstI site is located in the gene for $\beta$-lactamase, between the nucleotide triplets that code for amino acids 181 and 182 of that protein. This site was employed by Villa-Komaroff et al., supra, in their synthesis of protein displaying rat proinsulin antigenic determinants. One of the two HindII endonuclease recognition sites is between the triplets coding for amino acids 101 and 102 and one of the several Taq sites at the triplet coding for amino acid 45 of $\beta$-lactamase in pBR322. In similar fasion, the EcoRI site and the PvuII site in this plasmid lie outside of any coding region, the EcoRI site being located between the genes coding for resistance to tetracycline and ampicillin, respectively. This site was employed by Itakura et al. and Goeddel et al. in their recombinant synthetic schemes, supra. These sites are well recognized by those of skill in the art. It is, of course, to be understood that a cloning vehicle useful in this invention need not have a restriction endonuclease site for insertion of the chosen DNA fragment. Instead, the vehicle could be joined to the fragment by alternative means.

The vector or cloning vehicle and in particular the site chosen therein for attachment of a selected DNA fragment to form a recombinant DNA molecular is determined by a variety of factors, e.g., number of sites susceptible to a particular restriction enzyme, size of the protein to be expressed, susceptibility of the desired protein to proteolytic degradation by host cell enzymes, contamination of the protein to be expressed by host cell proteins difficult to remove during purification, expression characteristics, such as the location of start and stop codons relative to the vector sequences, and other factors recognized by those of skill in the art. The choice of a vector and an insertion site for a particular gene is determined by a balance of these factors, not all selections being equally effective for a given case.

Although several methods are known in the art for inserting foreign DNA into a cloning vehicle or vector to form a recombinant DNA molecule, the method preferred in accordance with this invention is described in Villa-Komaroff et al., supra, and displayed in FIG. 1. This method is characterized by digesting the plasmid (in particular pBR322) with that restriction enzyme specific to the site chosen for the insertion (in particular PstI) and adding dGMP tails to the termini by terminal transferase. dGMP tails are added to the 5' termini of the cut plasmid to regenerate the PstI site and permit linkage to a cDNA fragment carrying the complementary tails. In similar fashion, the double-stranded cDNA is elongated by the addition of dCMP tails to the 3' termini to allow joining to the tailed plasmid. The tailed plasmid and cDNA are then annealed to insert the cDNA in the appropriate site of the plasmid and to circularize the hybrid DNA, the complementary character of the tails permitting their cohesion (FIG. 1). The resulting recombinant DNA molecule now carries a gene at the chosen restriction site (FIG. 1).

Of course, other known methods of inserting DNA sequences into cloning vehicles to form recombinant DNA molecules are equally useful in this invention. These include, for example, direct ligation, synthetic linkers, exonuclease and polymerase-linked repair reactions followed by ligation, or extension of the DNA strand with DNA polymerase and an appropriate single stranded template followed by ligation.

It should, of course, be understood that the nucleotide sequences or cDNA fragment inserted at the selected site of the cloning vehicle may include nucleotides which are not part of the actual structural gene for the desired polypeptide or may include only a fragment of the complete structural gene for the desired protein. It is only required that whatever DNA sequence is inserted, a transformed host will produce a polypeptide having a biological or immunological activity of HIF or that the DNA sequence itself is of use as a hybridization probe to select clones which contain DNA sequences useful in the production of polypeptides having an immunological or biological activity of HIF.

The cloning vehicle or vector containing the foreign gene is employed to transform a host so as to permit that host to express the protein or portion thereof for which the hybrid DNA codes. The selection of an appropriate host is also controlled by a number of factors recognized by the art. These include, for example, compatibility with the chosen vector, toxicity of proteins encoded by the hybrid plasmid, ease of recovery of the desired protein, expression characteristics, biosafety and costs. A balance of these factors must be struck with the understanding that not all hosts may be equally effective for expression of a particular recombinant DNA molecule.

In the present synthesis, the preferred cloning vehicle is the bacterial plasmid pBR322 and the preferred restriction endonuclease site therein is the PstI site (FIG. 1). The plasmid is a small (molecular weight approx. 2.6 megadaltons) plasmid carrying resistance genes to the antibiotics ampicillin (Amp) and tetracycline (Tet). The plasmid has been fully characterized (F. Bolivar et al., "Construction And Characterization Of New Cloning Vehicles II. A Multi-Purpose Cloning System", *Gene*, pp. 95–113 (1977); J. G. Sutcliffe, "pBR322 Restriction Map Derived From the DNA Sequence: Accurate DNA Size Markers Up To 4361 Nucleotide Pairs Long", *Nucleic Acids Research*, 5, pp. 2721-28 (1978)).

Insertion of the DNA product in this site provides a large number of bacterial clones each of which contains one of the DNA genes or fragments thereof present in the DNA product previously prepared. Again, only a very few of these clones will contain the gene for IF or fragments thereof (FIG. 1). The preferred host in accordance with this invention is *E. coli* HB 101. Other experiments were conducted with *E. coli* X1776, a host described in British patent 1,516,458 and placed on deposit with the American Type Culture Collection, Rockville, Md., USA, where it has been assigned ATCC No. 31244.

1. Preparation of PstI-Cleaved, dGMP-elongated pBR322

Plasmid pBR322 (20 μg) was digested with 21 units PstI endonuclease (MRE Porton Downs or New England Biolabs) in 150 μl 10 mM Tris-HCl (pH 7.5), 6 mM $MgCl_2$, 50 mM NaCl, 6 mM 2-mercaptoethanol, 200 mg/μl bovine serum albumin ("BSA") (Calbiochem). After 2 h at 37° C., the mixture was extracted with 1 vol phenol-chloroform (1:1) and 1 vol ether ane precipitated with ethanol.

Addition of homopolymeric dGMP tails (FIG. 1) by terminal deoxynucleotidyl transferase (TdT) (purified according to F. J. Bollum, "Deoxynucleotide Polymerizing Enzymes From Calf Thymus Gland", in *Methods in Enzymology*, (L. Grossman and K. Moldave, eds.), Academic Press, New York, 128, pp. 591–611 (1968)) was done in a 328-μl reaction volume containing 100 mM sodium cacodylate (pH 7.2), 10 mM $NaH_2PO_4$, 5 mM $MgCl_2$ 1 mM dGTP, 50 μg/μl BSA, and 3–6 units of TdT (purified as above) per ug of DNA. Incubation was at 37° C. for 20 min. EDTA was added to 10 mM and the mixture extracted as above and dialyzed for 2 days against TNE buffer.

2. Preparation of dCMP-elongated DNA

Double-stranded DNA was elongated with dCMP residues by standard procedures (E.g., Villa-Komaroff et al., supra). 150 ng of the double-stranded cDNA described above were incubated in 8 μl 100 mM sodium cacodylate (pH 7.2), 2.5 mM $CoCl_2$, 50 μg/μl BSA, 0.1 mM dCTP containing 3–6 units of purified TdT per μg of DNA for 8 min at 27° C. and then frozen at −20° C. As before, the dCMP-elongated DNA is a mixture of different species, only a very few of which are IF-related (FIG. 1).

3. Preparation of $Ca^{++}$-Treated *E. coli* X1776

A single colony of *E. coli* X1776 was inoculated into 100 ml tryptone medium (C. Weissmann and W. Boll, "Reduction of Possible Hazards In The Preparation of Recombinant Plasmid DNA", *Nature*, 261, pp. 428-29 (1976), supplemented with 100 μg/ml diaminopimelic acid (Koch-Light Laboratories), 10 μg/ml nalidixic acid (Calbiochem) and 10 μg/ml tetracycline (Achromycin ®, American Cyanamid). The culture was grown at 37° C. to an apparent optical density of 0.6 at 650 nm ($OD_{650}$) (as measured in a Beckman DB spectrophotometer) and chilled in ice for 30 min. The culture was then sedimented at 4000 rpm in a Sorvall H4 swinging bucket rotor, the cells washed with 50 ml 10 mM NaCl, repelleted by centrifugation, and resuspended in 20 ml 100 mM $CaCl_2$. The suspension was cooled in ice for 30 min, pelleted by centrifugation and resuspended in 4 ml of 100 mM $CaCl_2$ and kept on ice overnight for use. *E. coli* HB101 was prepared for transformation by the method of M. Mandel and A. Higa, "Calcium-Dependent Bacteriophage DNA Infection", *J. Mol. Biol.*, 53, pp. 159–62 (1970). Aliquots (0.5 ml) were kept frozen at −70° C. and retained their activity for at least 3 months.

4. Annealing of dGMP-elongated pBR322 and dCMP-elongated DNA

The annealing of the tailed, PstI-cleaved pBR322 and tailed cDNA was as described in J. Van den Berg et al., "Comparison Of Cloned Rabbit And Mouse β-globin Genes Showing Strong Evolutionary Divergence Of Two Homologous Pairs Of Introns", *Nature*, 276, pp. 37–44 (1978). 8 ng of dCMP-elongated DNA product were mixed with 22 ng of dGMP-elongated PstI-cleaved pBR322 in 50 μl TNE buffer. Incubation was for 4 successive 1 h stages at 65° C., 46° C., 37° C. and 20° C. 20 μl 100 mM Tris-HCl (pH 7.5), 100 mM CaCl₂, 100 mM MgCl₂ and 50 μl TNE buffer were added and the mixture cooled in ice for 20 min.

The product is, of course, a large mixture of different recombinant DNA molecules and some cloning vehicles without inserted DNA sequences. However, each recombinant DNA molecule contains a cDNA segment at the PstI site. Each such cDNA segment may comprise a gene or a fragment thereof. Only a very few of the cDNA segments code for IF or a portion thereof (FIG. 1). The vast majority code for one of the other proteins or portions thereof whose mRNA's were part of the poly(A) RNA used in the process of this invention (FIG. 1).

5. Transfection Of *E. coli* X1776 With The Annealed Hybrid Plasmids

The transfection of *E. coli* X1776 with the mixture of recombinant DNA molecules was as described in J. Van den Berg et al., supra. P3 containment facilities were used for the transfection process and all subsequent steps in which the resulting transformed bacteria were handled. The annealed pBR322 recombinant DNA molecules were added to 100 ul of Ca⁺⁺-treated *E. coli* X1776, prepared previously, and the mixture cooled in ice for 20 min, heated at 20° C. for 10 min, and 0.6 ml tryptone medium added. The mixture was plated onto 2 tryptone medium agar plates supplemented as above. Transfection efficiency was 3.3×10⁴ colonies per ug of annealed pBR322 transfecting DNA; native pBR322 gave 3×10⁶ colonies per μg.

Since plasmid pBR322 includes the gene for tetracycline resistance, *E. coli* hosts which have been transformed with a plasmid having that gene intact will grow in cultures containing that antibiotic to the exclusion of those bacteria not so transformed. Therefore, growth in tetracycline-containing culture permits selection of hosts transformed with a recombinant DNA molecule or recyclized vector.

After 48 h at 37° C., individual colonies were picked and suspended in 100 μl tryptone medium (supplemented as above) in the wells of microtiter plates (Dynatech). After incubation at 37° C. overnight, 100 μl 40% glycerol were mixed into each well. The plates were stored at −20° C. and a library of 100,000 individual clones of transformed *E. coli* X1776 was prepared.

Figure 2:
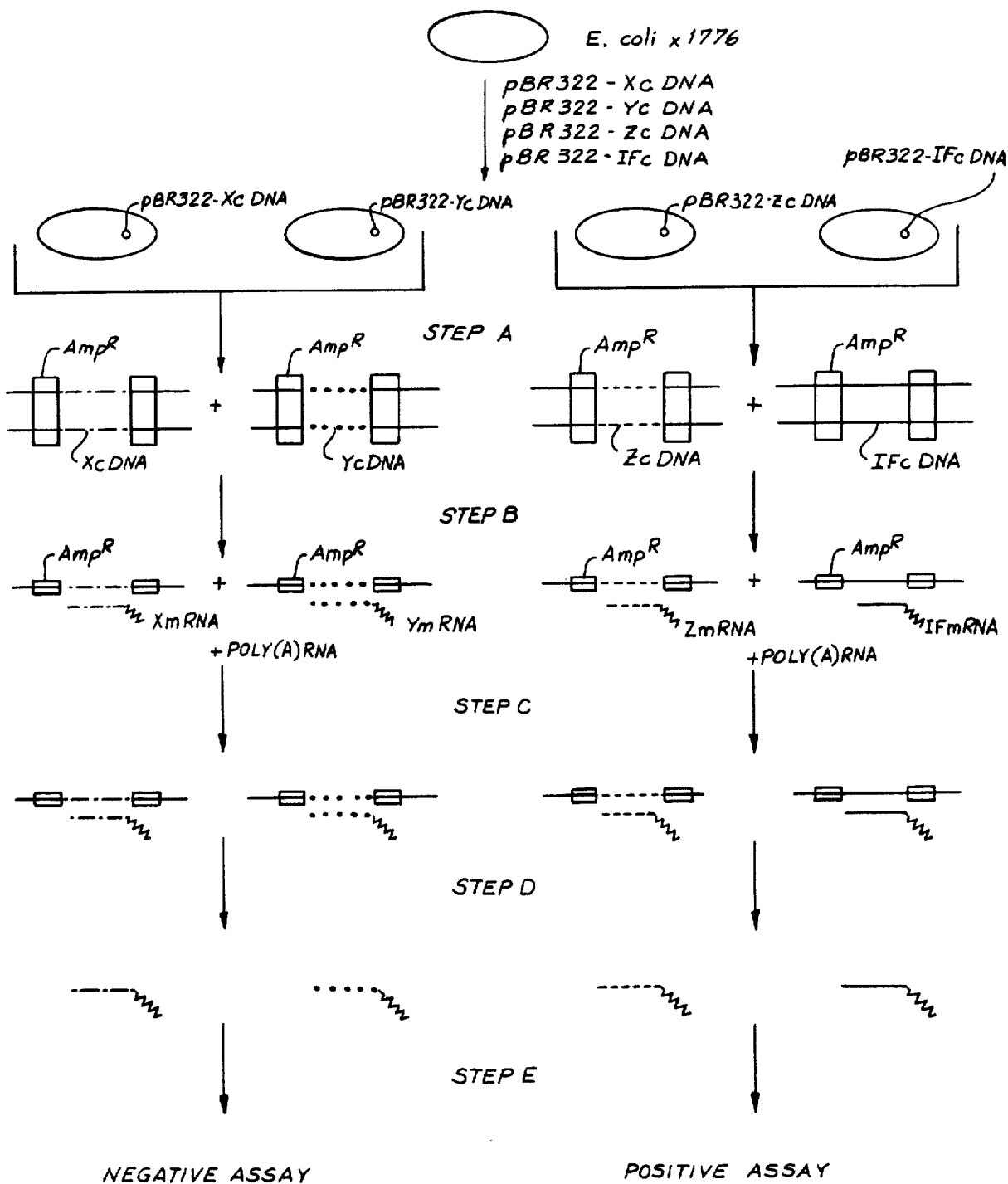
FIG. 2 is a schematic outline of the initial clone screening process of this invention.

These 100,000 clones contain a variety of recombinant DNA molecules representing complete or partial copies of the mixture of mRNAs in the poly(A) RNA preparation from IF-producing leukocytes (FIG. 2). The majority of these will contain only a single recombinant DNA molecule. Only a very few of these recombinant DNA molecules are related to IF. Accordingly, the clones must be screened to separate the IF-related clones from the others.

SCREENING FOR A CLONE CONTAINING IFcDNA

There are several approaches to screen for bacterial clones containing interferon cDNA ("IFcDNA"). These include, for example, RNA selection hybridization (Alwine et al., infra), differential hybridization (T. P. St. John and R. W. Davis, "Isolation of Galactose-Inducible DNA Sequences from Saccharomyces Cerevisiae by Differential Plaque Filter Hybridization", *Cell*, 16, pp. 443–452 (1979); Hoeijmakers et al., infra), hybridization with a synthetic probe (B. Noyes et al., "Detection and Partial Sequence Analysis of Gastrin mRNA by Using An Oligodeoxynucleotide Probe", *Proc. Natl. Acad. Sci. USA*, 76, pp. 1770–1774 (1979)) or screening for clones that produce the desired protein by immunological (L. Villa-Komaroff et al., supra) or biological (A. C. Y. Chang et al., supra) assays. We have chosen RNA selection hybridization as being the most convenient and promising method for primary screening.

A. RNA Selection Hybridization Assay

1. Overview Of The Initial Assay

Referring now to FIG. 2, recombinant DNA was isolated from a culture of a mixture of 512 clones from the above library of clones (two mixtures of 2 clones shown in FIG. 2) (Step A). The reason for selecting this batch size will be explained below. The recombinant DNA molecules were cleaved, denatured and hybridized to leukocyte poly(A) RNA containing IFmRNA prepared as before (Step B). All recombinant DNA molecule-poly(A) RNA hybrids were separated from the non-hybridized poly(A) RNA (Step C). The poly(A) RNA was recovered from the hybrids and purified (Step D). The recovered RNA was assayed for IFmRNA activity as above (Step E). If, and only if, the mixture of recombinant DNA molecules contains a recombinant DNA molecule having an inserted nucleotide sequence capable of hybridizing to the IFmRNA in the poly(A) RNA under stringent hybridization conditions, will the mRNA released from that hybrid cause the formation of interferon in oocytes, because mRNA released from any other recombinant DNA molecule-poly(A) RNA hybrid will not be IF-related. If a group of 512 clones gave a positive response, the clones were regrouped in 8 lots of 64, and each lot assayed as before. This process was continued until a single clone responding to this assay was identified.

There is no assurance that the recombinant DNA molecules and bacterial clone transformed therewith, which are thus identified, contain the complete IFcDNA sequence of IF or even that the DNA sequence actually codes for IF. However, the recombinant DNA molecules will certainly contain extensive nucleotide sequences complementary to the IFmRNA coding sequence. Therefore, the recombinant DNA molecule may at least be used as a source of a probe to screen rapidly other recombinant DNA molecules and clones transformed with them to identify further sets of clones which may contain an authentic and complete IF nucleotide coding sequence.

2. Theoretical Considerations

The conditions for the hybridization (Step B) are critical. The absolute concentrations and the ratio of recombinant DNA molecule and poly(A) RNA must be chosen so as to take into consideration reaction rate and stoichiometry. The proper choice is difficult to make, because the proportion of IFmRNA in the poly(A) RNA is not known. In order to assure controlled and adequate kinetics, the hybridization was carried out under conditions where the concentration of DNA sequences from the recombinant DNA molecules was in excess as compared to the estimated IFmRNA concentration. In a mixture of 512 possible different recombinant DNA molecules, an IF-related DNA sequence ("IFR DNA") will either not occur (giving a negative assay), or it will constitute at least about 1/512 of the recombinant DNA molecules. The concentration of the recombinant DNA molecule mixture and therefore the concentration of the IFR DNA, if any, can thus be adjusted in the hybridization step to ensure adequate hybridization rates. In addition, the amount of the IFR DNA in the reaction mixture must be sufficient to bind enough IFmRNA from the poly(A) RNA to allow detection of IF after injection into oocytes of the mRNA recovered from the recombinant DNA molecule-poly(A) RNA hybrid.

In order to detect IF by the assays available, its concentration should be 100 IU/ml or higher. Because 0.5 ml aliquots are required for replicate determinations, 50 IU should be generated in the oocytes. The poly(A) RNA from induced leukocytes, used previously, generates about 500 IU IF upon injection of 1 μg into oocytes. Therefore, at least 0.1 μg poly(A) RNA has to be injected to generate the needed 50 IU. Model experiments with rabbit globin mRNA and rabbit β-globin cDNA clones showed that the overall recovery of $^{125}$I-globin mRNA in the oocyte relative to $^{125}$I-globin mRNA added to the hybridization mix was about 10%, and the recovery of mRNA activity about 5%. Therefore, at least $0.1/0.05 = 2$ μg of leukocyte poly(A) RNA should be used for the hybridization assay. To ensure an adequate safety margin, 12 μg of poly(A) RNA were used per assay.

To calculate how much DNA from the recombinant DNA molecules is required to bind the IFmRNA in 12 μg of poly(A) RNA, the IFmRNA content of poly(A) RNA was estimated. One μg of poly(A) RNA generates 500 IU of IF. The specific activity of IF lies between $2 \times 10^8$ and $10^9$ IU/mg protein. 500 IU of IF therefore correspond to between $500/2 \times 10^8 = 2.5 \times 10^{-6}$ mg (2.5 ng) and $500/10^9 = 5 \times 10^{-7}$ mg (0.5 ng) of interferon.

The relationship between the amount of IFmRNA injected into an oocyte and the amount of IF produced is unknown. In the case of β-globin mRNA, about 30 molecules of protein per molecule mRNA are produced per hour; this value is about 6 for β-globin (J. B. Gurdon et al., "Message Stability In Injected Frog Oocytes: Long Life of Mammalian And β-Globin Messages", *J. Mol. Biol.*, 80, pp. 539-51 (1973)). Assuming an average value of 20 for IF, a molecular weight of 18000 for LeIF and a molecular weight of 330,000 for IFmRNA, then 26 mg $(18000/330000 \times 20 \times 24)$ of IF should be produced in 24 h per mg of IFmRNA injected. If the specific activity of IF is $2 \times 10^8$/mg ($2 \times 10^2$ IU/ng), then 1 ng IFmRNA will yield $26 \times 2 \times 10^2 = 5.2 \times 10^3$ IU of IF. If the specific activity is $10^9$/mg ($10^3$ IU/ng), the amount of IF produced would be $2.6 \times 10^4$ IU. Because 1 μg of leukocyte poly(A) RNA yields 500 IU of IF, under the above assumed conditions, the concentration of IFmRNA in 1 μg poly(A) RNA would fall between 0.1 ng to 0.02 ng and the proportion of IFmRNA in leukocyte poly(A) RNA would lie between 1:10,000 and 1:50,000. Therefore, 12 82 g of poly(A) RNA contains about 1.2 ng to 0.2 ng IFmRNA.

Should the translation ratio of the IFmRNA in the oocytes be lower by an order of magnitude than the average for globin mRNA, the IFmRNA content of the poly(A) RNA would be 10 times higher than calculated above, or between about 1:1000 to 1:5000. And, 12 μg of poly(A) RNA would then contain about 12 ng to 2 ng of IfmRNA. On the other hand, should the translation ratio of the IFmRNA in the oocytes be higher by an order of magnitude than the average for globin mRNA, the IFmRNA content of the poly(A) RNA would be 10 times lower than calculated above, or between about 1:100,000 and 1:500,000. And, 12 μg of poly(A) RNA would then contain 0.1 ng to 0.02 ng IFmRNA.

Plasmid pBR322 has 4361 b.p. The complete cDNA of IFmRNA would add about 800-1000 b.p. to pBR322 on formation of pBR322-IFcDNA to a total of about 5200-5400 b.p. Its molecular weight would thus be about 12 times $(2 \times 5200/800)$ that of the IFmRNA alone. Therefore, in order to bind the IFmRNA calculated above to be present in 12 ug poly(A) RNA required for the assay, an amount of recombinant DNA molecules equal to 12 times the amount of the IFmRNA will be required (stoichiometric amount).

Because the IFmRNA content of the poly(A) RNA used to prepare the recombinant DNA molecules had been increased 10 to 40-fold over that of the crude poly(A) RNA, the group of 512 clones should have 10 to 40 times more clones containing the desired IFmRNA than calculated from the above.

If IFmRNA is 1 part in 1000 of the crude poly(A) RNA, then 12 μg of poly(A) RNA contain 12 ng IFmRNA and the stoichiometric amount of IFcDNA plasmid is 144 ng. Since a group of 512 clones will contain at least 5 with IFcDNA inserts, the amount of total hybrid plasmid DNA required is 14.8 μg $(144 \times 512/5 \times 10^{-3})$. If IFmRNA is 1 part in 10,000, then 12 μg of poly(A) RNA contain 1.2 ng IFmRNA and the amount of IFcDNA plasmid required is 14.4 ng. A group of 512 clones will contain either 0 or 1 IFcDNA insert, so that the amount of total hybrid plasmid DNA required is 7.4 μg $(14.4 \times 512 \times 10^{-3})$. If IFmRNA is 1 part in 100,000, then the amount of total hybrid plasmid DNA required is 0.74 μg $(1.44 \times 512 \times 10^{-3})$. In order to ensure that the hybridization reaction will proceed under DNA excess conditions (i.e., excess recombinant DNA as compared to poly(A) RNA), 20 μg of the mixture (about 1.4 to 30-fold excess) was chosen for the assay.

Hybridization must be conducted under conditions which ensure (a) that the hybridized portion of the poly(A) RNA is recovered intact and in a biologically active form, (b) that non-specific DNA-mRNA association is prevented, and (c) that the hybridization reaction goes to at least 75% completion. These conditions are most likely to be met by hybridization in 80% formamide, 0.4M NaCl (J. Casey and N. Davidson, "Rates of Formation and Thermal Stability of RNA:DNA and DNA:DNA Duplexes At High Concentrations of Formamide", *Nucleic Acids Res.*, 4, pp. 1539-52 (1977)). In this solution, hybridization can be conducted at about 40° C. (rather than the 60°–70° C. required when formamide is omitted). Lower temperatures are preferred to minimize damage to the poly(A) RNA. We chose a hybridization temperature of 56° C. This is about 3° below the $T_{1/2i}$ (J. Casey and N. Davidson, supra) and about 10°–13° below $T_{1/2d}$ (Hamaguchi & Geidushek, *J. Amer. Chem. Soc.*, 84, p. 1329). Therefore, this temperature should not allow hybridization of sequences with less than about 87% homology, since a 1% mismatch lowers the $T_{1/2d}$ by 1° (T. F. Bonner et al., "Reduction In The Rate of DNA Reassociation By Sequence Divergence", *J. Mol. Biol.*, 81, pp. 123-35 (1973)).

In the present hybridization, self-hybridization of DNA is not a major problem because the mixture of DNA's being used consists of the same vector (pBR322) and a variety of cDNA inserts. Therefore, most of the DNA sequences will be heteroduplexes in which the inserts are available for hybridization to poly(A) RNA. It is very unlikely that complementary cDNA inserts which form part of different duplexes will interact because of topological constraints. In any event, DNA:DNA reassociation is minimized under the reaction conditions used (J. Casey and N. Davidson, supra).

To determine the hybridization time required to ensure at least 75% reaction, a second order rate equation was employed:

$$t = \frac{\ln\left[\dfrac{Co - Ro + Ro\left(1 - \dfrac{R}{Ro}\right)}{\left(1 - \dfrac{R}{Ro}\right)Co}\right]}{k_R(Co - Ro)} = 3.9\ h$$

where:
R = molar nucleotide concentration of hybridized RNA
Co = molar nucleotide concentration of initial DNA to be hybridized
Ro = molar nucleotide concentration of initial RNA to be hybridized
$k_R$ = rate constant for RNA-DNA hybridization
t = time (sec)
and:
R/Ro = 0.75 (75% reaction completion)
$k_R = 472$ ($k_R = 1/12\ k_d$ (J. Casey and N. Davidson, supra)
where: $k_d$ = second order rate constant for DNA under the chosen conditions of hybridization
and: $k_d = 1.7 \times 10^5 \times L^{1/2} \times N^{-1}$ (J. R. Hutton and J. G. Wetmur, "Renaturation of Bacteriophage φX174 DNA-RNA Hybrid: RNA Length Effect And Nucleation Rate Constant", *J. Mol. Biol.*, 77, pp. 495-500 (1973))
L = 900 (chain length in b.p.; about 900 are present in the full IFcDNA insert)
N = 900 (complexity in b.p. of the hybrid chain; here the complexity is 900 because the 900 nucleotides of the IFmRNA join with the complementary 900 nucleotides of the IFcDNA insert)
$Co = 2.5 \times 10^{-7}$ (Based on a 40 μl solution containing the previously determined 20 μg of recombinant DNA molecules to be used in the assay, again assuming that the IFcDNA insert will be 1/12 of a recombinant DNA molecule and will occur in at least 1 of the 512 clones, and assigning 662 as the average molecular weight of one DNA base pair)
$Ro = 8.7 \times 10^{-8}$ (Based on a 40 μl solution containing the previously determined 12 μg of poly(A) RNA to be used in the assay, again assuming that the poly(A) RNA contains 1:10,000 parts IFmRNA (given the large excess of DNA a different proportion will have little effect on the rate of hybridization) and assigning 343 as the average molecular weight of one ribonucleotide of RNA)

3. Execution Of The Initial Assay

Step A—Preparation and Cleavage of the Recombinant DNA Molecule Mixture

The desired number of bacterial clones was inoculated onto tryptone medium agar plates supplemented as above, by transferring to it an aliquot from each microtiter well with use of a mechanical device. After incubation at 37° C., each clone had given rise to a colony of several mm diameter. All colonies were washed off the plate(s) and pooled to give an inoculum used to inoculate 1 l of tryptone medium supplemented as above in a 2 l Erlenmyer flask. The culture was shaken at 37° C. to an apparent $OD_{650}$ of about 0.8 (estimated visually). One volume of supplemented tryptone medium and chloramphenicol to 170 μg/ml were added to the culture which was further shaken at 37° C. for 16 h. 20 ml chloroform were added and the culture shaken again for 10 min at 37° C. to kill the bacteria (C. Weissmann and W. Boll, supra). The culture was decanted from the chloroform and the cells were harvested by centrifugation (Sorvall GS3 rotor) for 15 min at 6000 rpm and 4° C. About 1–2 g of cells were obtained for each 1-liter preparation. The cells were suspended in 30 ml 20 mM Tris-HCl (pH 7.5), centrifuged for 20 min at 5000 rpm and 4° C. (Sorvall SW rotor) and resuspended in 30 ml 50 mM Tris-HCl (pH 7.5). 0.25 vol of lysozyme solution (10 mg/ml in 50 mM Tris-HCl (pH 7.5)) were added and after cooling for 10 min at 0° C. 0.33 vol (based on the vol of the original 50 mM Tris-HCl-culture suspension) 0.5M EDTA (pH 8.0) were gently mixed in without shaking. After another 10 min at 0° C., 1/16 vol (again based on the original volume) of 2% Triton X-100 were added. After 60 min, the sample was centrifuged for 60 min at 10,000 rpm and 0° C. in a Sorvall SW rotor. The supernatant was transferred to a beaker containing a magnetic stirrer, and 3M NaOH was added with stirring until a pH of 12.5 was reached, as measured at 20° C., using a glass electrode and an Orion Research model 601 pH meter, standardized with Beckman pH 10 Carbonate Buffer Standard (No. 3505). After stirring 10 min at 20° C., the pH was adjusted to 8.5. After 3 min further stirring 1/9 vol 5M NaCl and 1 vol phenol (distilled and equilibrated with 9.5M NaCl) were added and vigorous stirring continued for 5 min. The phases were separated by centrifugation (GSA Sorvall rotor) at 10,000 rpm and 0° C. for 10 min. The supernatant containing Form I DNA (circular double-stranded DNA) was carefully removed from the interphase (which contains single-stranded DNA) and extracted 3 times with chloroform. (Phenol must be largely removed at this step). The Form I DNA fraction will contain those recombinant DNA molecules (pBR322-cDNA insert) originally used in transforming those host cells which form part of the 512 clones chosen for assay.

Pancreatic RNAase A (5 mg/ml, preheated 10 min at 85° C.) was added to the Form I DNA to a concentration of 20 μg/ml and the mixture incubated 60 min at 37° C. 1/5 vol 5M NaCl were added and the mixture adjusted with 30% polyethylene glycol 6000 (Union Carbide, autoclaved 20 min at 120° C.) up to a final concentration of 7.5% PEG. After 2–16 h at −10° C., the precipitate was collected in a Sorvall SW Rotor for 20 min at 8,000 rpm and 0° C., dissolved in 0.075M NaCl, 0.0075M Na-citrate to an absorbance of 20 at 260 nm, and adjusted to 0.5% SDS. The solution was incubated for 30 min at 37° C. with 0.5 mg/ml Pronase (self-digested at 20 mg/ml, 2 h at 37° C.) and extracted 3 times with 1 vol distilled phenol and 2 times with 1 vol chloroform. The sample (up to 2 ml of a 1 mg/ml DNA solution) was centrifuged through a 5 to 23% sucrose gradient in 50 mM Tris-HCl (pH 7.5), 1 mM EDTA for 15 h at 21,000 rpm and 15° C. using an SW 27 Beckman Rotor. Fractions were collected and the $OD_{260}$ monitored. DNA-containing fractions were pooled and the DNA precipitated with sodium acetate and ethanol. 20 to 100 ug of the Form I DNA mixture were recovered by centrifugation.

Twenty μg of purified Form I DNA were digested in 150 μl 10 mM Tris-HCl (pH 7.5), 6 mM $MgCl_2$, 50 mM NaCl, 6 mM 2-mercaptoethanol, 200 μg/ml BSA or gelatin and 20 units HindIII (New England Biolabs). The HindIII restriction enzyme cleaves the Form I DNA at a site within the pBR322 moiety (It is unlikely that the cDNA moiety is also cleaved, but if it is, the assay should not be substantially affected). After 2 h at 37° C., an aliquot (1%) was analyzed by electrophoresis through a 1% agarose gel in 50 mM Tris-acetate (pH 7.8), 2 mM EDTA for 1 h at 50 mA to ascertain whether digestion was complete. If digestion was not complete, more HindIII was added and incubation continued for 2 h. When the Form I DNA was converted totally to linear molecules, Pronase (Calbiochem), EDTA and SDS were added to 0.5 mg/ml, 10 mM and 0.5% respectively. After 30 min at 37° C., the solution was extracted with 30 μl phenol-chloroform (1:1). The organic phase was washed with 50 μl 20 mM Tris-HCl (pH 7.5), 1 mM EDTA, and the combined aqueous phases extracted 3 times with ether, filtered through a 0.1-ml Chelex column, collected in an EDTA-boiled Pyrex ® tube and precipitated with 1/10 vol 3M sodium acetate and 2.5 vol ethanol. After standing overnight at −20° C., the DNA was collected by centrifugation.

Step B—Hybridization of the DNA with Poly(A) RNA

Two hybridization mixtures were prepared. Mixture I contained 4 μl of 10-fold concentrated hybridization buffer (4M NaCl, 0.1 PIPES (pH 6.4, 1,4 piperazinediethane sulfonic acid, Sigma), 50 mM EDTA, 0.5 μl (about 5 ng $^{125}$I-globin mRNA (5000 cpm) and 6 μl induced leukocyte poly(A) RNA (2 μg/μl), an amount sufficient to generate 6000 IU of IF when injected into oocytes. Mixture II contained 10 μg of the HindIII digested Form I DNA from above and 0.1 μg of PstI-digested Z-pBR322(H3)/Rc β G-4.13 (a pBR322 derivative that contains the β-globin sequence in the HindIII site) (Mantei et al., "Rabbit β-globin mRNA Production in Mouse L Cells Transformed With Cloned Rabbit β-globin Chromosomal DNA", *Nature*, 281, pp. 40–46 (1979)). The $^{125}$I-globin mRNA in mixture I and the β-globin DNA in mixture II serve as internal positive controls for the hybridization assay. Both mixtures were dried in a stream of nitrogen gas. 40 ul of 80% formamide were added to the residue of mixture II and the solution was denatured for 10 min at 100° C. and chilled quickly in ice. The denatured solution was used to dissolve the residue of mixture I and the resulting solution incubated at 56° C. for 4 h.

Step C—Separation Of Hybridized Poly(A) RNA-DNA From Non-Hybridized Poly(A) RNA

After dilution to 1 ml with cold 0.9M NaCl, 0.09M Na-citrate and formamide (100%) to 4% (by volume) the solution was filtered at 0.5 ml/min through a Millipore filter (0.45 μm pore size), the filter having been first tested for its capacity to retain RNA-DNA hybrids, because not all filters obtained from the manufacturer were equally efficient.

Step D—Purification of Hybridized Poly(A) RNA

The above filter, with poly(A) RNA hybrids attached, was immersed in 1 ml 0.15M NaCl, 0.015M Na-citrate, 0.5% SDS for 10 min at 37° C., rinsed with 50 mM Tris-HCl (pH 7.5), 10 mM $MgCl_2$, 2 mM $CaCl_2$ and placed in 0.6 ml of fresh buffer. After the addition of 5 μl iodoacetate-treated DNAase (5 mg/ml) (S. B. Zimmermann and G. Sandeen, *Anal. Biochem.*, 14, p. 269 (1966); P. A. Price et al., "Alkylation of A Histidine Residue At The Active Site Of Bovine Pancreatic Deoxyribonuclease", *J. Biol. Chem.*, 244, pp. 924–32 (1969)), the filter was incubated at 37° C. for 10 min.

The filter was removed and the solution extracted with 1 vol phenol and 1 vol ether and passed through a 0.1-ml Chelex column. 5 μg of carrier RNA (purified yeast RNA) were added to the solution and the RNA precipitated with sodium acetate and ethanol. The precipitate was collected by centrifugation at 10,000 xg, dissolved in 100 μl 1 mM EDTA, heated for 90 sec at 100° C., and TNE and SDS added to 2×TNE and 0.5% SDS. The RNA was adsorbed to a 100-μl oligo(dT) cellulose column, eluted with four washes of 0.3 ml distilled water and precipitated with sodium acetate and ethanol. After 16 h at −20° C. the precipitated RNA was separated by centrifugation and dissolved in 2 μl TNK buffer.

Step E—Determination Of IFmRNA Activity

The poly(A) RNA solution from above was injected into 40 oocytes (about 50 nl per oocyte). The oocytes were incubated at 23° C. for 24–48 hours, homogenized and centrifuged (or the incubation medium recovered) and assayed as described previously for IF.

4. Subsequent Assay-Hybridization To Filter-Bound DNA

Most subsequent assays of a recombinant DNA molecule from a single clone were carried out with DBM or DPT paper-bound DNA, because the assay conditions were no longer critical and the assay is more convenient. DPT paper gave lower backgrounds and was used preferentially. DBM paper was prepared as described (J. C. Alwine et al., "Method For Detection of Specific RNAs In Agarose Gels By Transfer To Diazobenzyl Oxymethyl-Paper And Hybridization With DNA Probes", *Proc. Natl. Acad. Sci. USA*, 14, pp. 5350–54 (1977)). APT paper was prepared by a procedure of B Seed (pers. commun.): Sheets of Whatman 540 paper (20 g) were agitated for 16 h at 20° C. with a mixture of 70 ml 0.5M NaOH, 2 mg/ml $NaBH_4$ and 30 ml 1,4-butanediol diglycidyl ether. The paper was then transferred to a solution of 10 ml 2-aminothiophenol in 40 ml acetone and agitated for 10 h. The paper was exhaustively washed with acetone, 0.1N HCl, H$_2$O, 0.1N HCl, H$_2$O and dried. APT paper was diazotized to DPT paper as described for the conversion of ABM to DBM paper (Alwine et al., supra).

DNA (up to 15 μg) was bound to 50 mm$^2$ diazotized ABM (DBM) or diazotized APT (DPT) paper as described by J. H. J. Hoeijmakers et al. "The Isolation Of Plasmids Containing DNA Complementary To Messenger RNA for Variant Surface Glycoproteins of Trypanosoma Brucei", Gene, in press, 1980) and set forth below.

Hybrid plasmid DNA was digested with endonuclease PstI, treated with 500 ug Pronase per ml, 0.5% SDS, and 10 mM EDTA for 30 min at 37° C., extracted with phenol and ether, passed through a 0.1-ml Chelex column, and precipitated with ethanol. The heat-denatured DNA (up to 5 ug, with a small amount of $^{32}$P-DNA added as tracer) was incubated overnight at 0° C. with 1 cm$^2$ DBM or DPT paper in 200 ul 25 mM potassium phosphate buffer (pH 6.5). Filters were washed three times for 5 min at room temperature with 50 mM potassium phosphate buffer (pH 6.5), 1% glycine and three times with 99% recrystallized formamide. A further incubation with 99% formamide for 2 min at 68° C. was followed by three washes in 50 mM potassium phosphate buffer (pH 6.5) at 20° C. and two washes in 0.4M NaOH at 37° C. for 10 min. About 40–60% of the radioactivity was retained on the filters. The filters were incubated for 3 h at 38° C. in pre-hybridization medium A, supplemented with 1% glycine, using 330 ul per filter. Medium A contains 50% formamide, 5×SSC, 0.04% polyvinyl pyrrolidone, 0.04% Ficoll (Pharmacia), 0.1% SDS, 25 ug poly(A) (P & L) and 100 μg yeast RNA (BDH, extracted six times with phenol and precipitated with ethanol). The filters were washed twice in medium A and then hybridized for 16 h at 38° C. with poly(A) RNA as indicated (usually 5–8 μg) in medium A under paraffin oil. The RNA was added as follows: one wet DNA filter was blotted and put in a sterile Petri dish, 20–40 μl of the RNA solution were pipetted on this filter and a second DNA filter (either a duplicate or a control) was put on top and the sandwich was covered with a sterile paraffin oil. After the hybridization the filters were successively washed in medium A (2 times), in a solution containing 1×SSC, 0.2% SDS, 1 mM EDTA (3 times, 10 min at 20° C. each), medium A (2 h at 38° C.) and in 50% formamide, 5×SSC, 0.1% SDS (3 times, 10 min at 20° C.). Hybridized RNA was eluted by heating for 1 min at 100° C. in 200 μl 10 mM Tris-HCl (pH 7.4), 1 mM EDTA and 0.1% SDS. The elution step was repeated twice, the eluates were combined and the RNA was precipitated with ethanol after addition of 2 μg yeast RNA (purified as above). The washed pellet was vacuum dried, dissolved in 3 μl H$_2$O and injected into oocytes. IF activity was assayed as above.

5. Results Of The RNA Selection Hybridization Assay

The assays from 8 groups of 512 clones (i.e., groups T, Y, j, K, ⊡, O, Σ and π were negative. The assays from 4 groups of 512 clones (i.e., groups I, δ N and λ) were positive, albeit not consistently. The positive assays are reported in the following format: IU/ml of IF produced by the RNA released from poly(A) RNA-DNA hybrid (assay from control hybridization using Z-pBR322(H3)/Rc β G-4.13, supra); the assays in which the experimental results were higher than the background control are underscored.

| Group | IU/ml |
|---|---|
| I | <60 (<60); 110 (<20); <110 (<110); <110 (<110); <35 (<35) |
| δ | 20 (<20) |
| N | 35 (<20); <110 (<110); 200 (<110) |
| λ | <60 (<60); 60 (<20); <110 (<110); <110 (<110) |

Group λ was subdivided into 8 subgroups of 64 clones and hybridized and assayed as before. The subgroups gave the following results, presented in the same format as above:

| Subgroup | IU/ml |
|---|---|
| λ-I | <35 (<35); <35 (<35) |
| λ-II | 130 (<30); <45 (<45) |
| λ-III | 225 (<35); 35 (<30); 35 (<30); 600 (<30); <20 (<20) |
| λ-IV | 85 (<35); <25 (<25) |
| λ-V | <35 (<35) |
| λ-VI | <35 (<35) |
| λ-VII | <35 (<35) |
| λ-VIII | <35 (<35) |

Subgroup λ-III was subdivided into 8 sets of 8 clones, and hybridized and assayed:

| Set | IU/ml |
|---|---|
| λ-III-1 | <20 (<20); <20 (60); 35 (<30) |
| λ-III-2 | <35 (<35); <30 (<30); 150 (<20); 600 (<35); 110 (60) |
| λ-III-3 | <25 (<25); <30 (<30) |
| λ-III-4 | 30 (<30); <20 (<20); <20 (60) |
| λ-III-5 | 30 (?) (<35); <20 (<20); <35 (60) |
| λ-III-6 | <30 (<30); <20 (<20) |
| λ-III-7 | <30 (<20) |
| λ-III-8 | <30 (<20) |

Because the first positive result was achieved with the set λ-III-4, the individual colonies of this set (designated A to H) were hybridized and assayed:
λ-III-4-B <35* (<35); <20 (60)
λ-III-4-C 35 (60); 60* (<35); 111* (<11); <11* (<11); 20 (<20)
Therefore, clone λ-III-4-C contains a recombinant DNA molecule capable of hybridizing IFmRNA.
* The DBM paper method was used in this assay The recombinant DNA molecule in this clone is designated: Z-pBR322(Pst)/HcIF-4C ("Hif-4C"), and the bacterial strain containing it: E. coli X1776 (Z-pBR322(Pst)/HcIF-4C ("E. coli Hif-4C"). This nomenclature indicates that the recombinant DNA molecule originated in Zurich (Z) and is plasmid pBR322 containing at the PstI site a HIF cDNA ("HcIF"); the particular recombinant DNA molecule being derived from clone λ-III-4-C ("4C").

RECLONING AND CHARACTERIZATION OF Z-pBR322(Pst)/HcIF-4C

Since primary clones of transformed cells occasionally contain more than one species of recombinant DNA molecule (Efstratiadis et al., "The Primary Structure Of Rabbit β-globin mRNA As Determined From Cloned DNA", Cell, 10, pp. 571–85 (1977)), Hif-4C was isolated from E. coli X1776 (Hif-4C) clones and purified as described above. Samples of Hif-4C and pBR322 were digested with PstI and analyzed by electrophoresis on a 1% agarose gel. Hif-4C gave two bands, one with the mobility of Pst-cleaved pBR322, the other with a mobility corresponding to about 320 b.p.

E. coli HB101 was transformed with the isolated Hif-4C as described above. Six clones of tetracycline-resistant, transformed bacteria were picked, small cultures prepared and Form I DNA purified and analyzed by PstI cleavage and agarose gel electrophoresis as before. All samples showed cleavage patterns identical to Hif-4C. One of these recloned recombinant DNA molecules was designated Z-pBR322(Pst)/HcIF-4c ("Hif-4c") and used for further experimentation. The lower case "c" designates a recloned DNA molecule.

To determine the capacity of Hif-4c and its cDNA insert to hybridize to IFmRNA, Hif-4c (115 μg) was digested to completion with 125 units of PstI, extracted with phenol and chloroform, and precipitated with ethanol as described above. An aliquot (10 μg) was 5' terminally labeled (to serve as a tracer in subsequent steps) by dissolving it in 100 μl 50 mM Tris-HCl (pH 7.5), passing it through a 0.1-ml Chelex 100 column and treating it with 0.6 units bacterial alkaline phosphatase for 1 h at 65° C. Tenfold concentrated TNE (40 μl) was added and the solution extracted 3 times with 1 vol phenol and 3 times with 1 vol chloroform. The DNA was precipitated with 2 vol ethanol at −20° C. overnight and collected by centrifugation. For further purification, the sample in 0.5 ml TNA was adsorbed to 0.25-ml DEAE cellulose (Whatman DE52, prewashed with 2 ml 150 mM NaCl, 50 mM Tris-HCl (pH 7.5), 2 mM EDTA) ("NET-buffer"), washed with 2 ml of NET buffer, eluted with 0.4 ml 1.5M NaCl, 20 mM Tris-HCl (pH 7.5), 2 mM EDTA and precipitated with ethanol as above. The DNA was incubated with $\gamma$-$^{32}$P-ATP (specific activity about 5000 Ci/mmole) and polynucleotide kinase, (A. M. Maxam and W. Gilbert, "A New Method For Sequencing DNA", Proc. Natl. Acad. Sci. USA, 74, pp. 560–564 (1977)) and purified by chromatography on a 3-ml Sephadex-G50 column in TNE. The eluted fractions were pooled and the $^{32}$P-DNA precipitated with ethanol as above; yield, about $10^7$ dpm.

The unlabeled PstI-cleaved Hif-4c DNA (90 ug) was mixed with $6 \times 10^5$ dpm of $^{32}$P-labeled PstI cleaved Hif-4c DNA from above and electrophoresed through a $10 \times 20 \times 0.7$ cm, 2% horizontal agarose gel in 50 mM Tris-acetate buffer (pH 7.8) using a 2.5 cm slot. An x-ray film was exposed to the gel and the position of the 320-bp fragment determined. The gel strip containing the radioactive band ($1.3 \times 10^5$ dpm) was cut out, crushed by pressing through a plastic 2-ml syringe and extracted overnight at 4° C. by agitation with ten times the gel vol of NET buffer. The DNA was adsorbed to a 0.1-ml hydroxyapatite column (prewashed with 1 ml NET buffer). The column was washed with 1 ml 0.1M K-phosphate buffer (pH 7.5) and the DNA eluted with 0.2 ml 1M K-phosphate buffer (pH 7.5). The eluate was diluted 10-fold with sterile distilled H$_2$O and the DNA adsorbed to and eluted from DEAE and precipitated with ethanol as described above. This DNA is called "Hif-4c fragment".

The Hif-4c fragment (120 ng) was bound to DPT paper (0.5 × 0.5 cm) as described above. As a control, 120 ng β-globin cDNA fragment excised with HindIII from the hybrid plasmid Z-pBR322(H3)Rc β G-4.13 (F. Meyer et al., "Transposition Of AT-linked, Cloned DNA From One Vector To Another", Experimentia, 35, p. 972 (1979); N. Mantei et al., supra) and processed similarly. Hybridization of duplicate filters to poly(A) RNA (in 20 μl), washing of the filters and recovery of the RNA from the filters were as described above. After injection into oocytes the following IF activities were detected:

| DNA fragment | amount of leukocyte poly (A) RNA* (μg) | time of hybridization | IF activity (IU/ml)** (duplicate assay) |
|---|---|---|---|
| Hif-4c | 2.5 | 16 h | 250; 100 |
| β-globin cDNA | 2.5 | 16 h | 4; 1 |
| Hif-4c | 7.5 | 16 h | 3000; 1000 |
| β-globin cDNA | 7.5 | 16 h | 4; 30 |
| Hif-4c | 7.5 | 5 h | 1000;1000 |
| β-globin cDNA | 7.5 | 5 h | 10; 1 |

*1 μg of this RNA gave 4600 IU/ml.
**Oocyte supernatant after 48 h incubation, assayed by cytopathic effect reduction (W. E. Stewart, II and S. E. Sulkin, supra).

Thus, Hif-4c contains an insert capable of hybridizing to IFmRNA.

IDENTIFICATION OF CLONES OF E. COLI CONTAINING RECOMBINANT DNA MOLECULES CROSS-HYBRIDIZING TO THE INSERT IN Hif-4c

Figure 3:
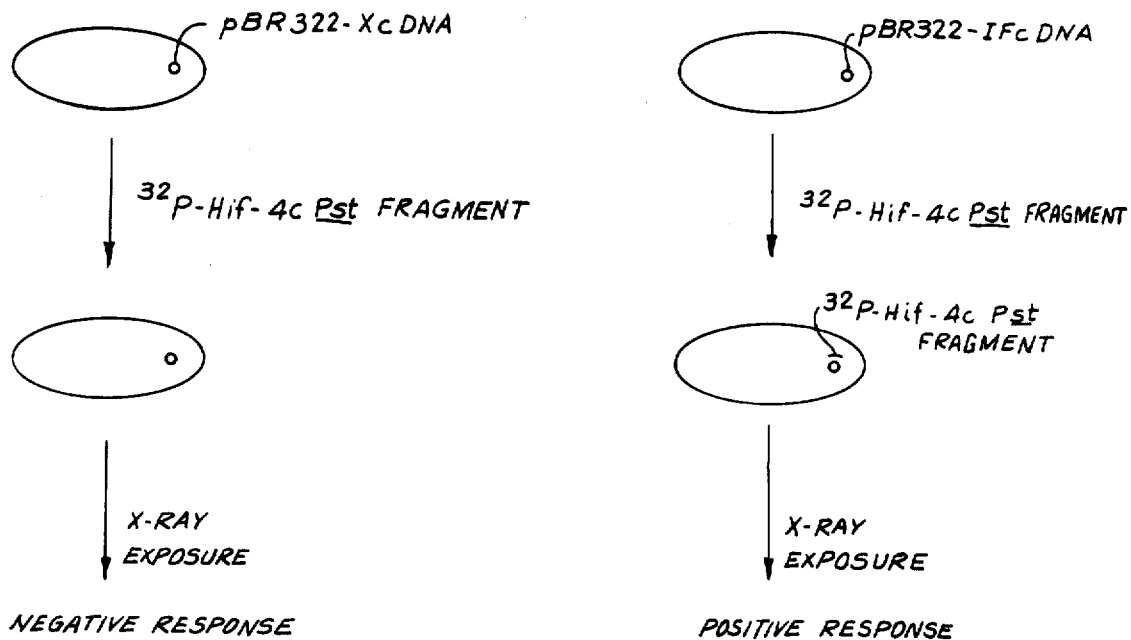
FIG. 3 is a schematic outline of one embodiment of a clone screening process using DNA sequences prepared in accordance with the invention.

Since the cDNA insert in recombinant DNA molecule Hif-4c was only about 320 b.p., or a third of the estimated size of IFmRNA, the purified Hif-4c fragment described above was used as a probe to screen for bacterial clones containing recombinant DNA molecules having related hybrid DNA inserts (FIG. 3).

The 64 bacterial clones constituting subgroup λ-III described above were stamped onto a Millipore membrane (8 cm diameter), placed on an agar plate (supplemented with diaminopimelic acid, nalidixic acid and tetracycline, as above) and incubated for 24 h at 37° C. The filter was placed onto a 0.75 ml drop of 0.5M NaOH and after 2–3 min transferred onto a paper towel to remove excess liquid; the step was repeated. The filter was neutralized, using 1M Tris-HCl (pH 7.5), and washed with 1.5M NaCl-0.5M Tris-HCl (pH 7.4) in a similar fashion as above and air dried. The filter was dipped in 0.3M NaCl, air dried and heated at 80° C. for 2 h in a vacuum.

Hif-4c Pst fragment (30 ng) was =P-labeled by nick translation (A. J. Jeffreys and R. A. Flavell, "The Rabbit β-Globin Gene Contains A Large Insert In The Coding Sequence", Cell, 12, pp. 1097–1108 (1977)) using α-$^{32}$P dATP and α-$^{32}$P dCTP (specific activity, 40 Ci/mmole each). The filter bearing the λ-III colonies was prehybridized in 4×SET (SET is 0.15M NaCl, 30 mM Tris-HCl (pH 8.0), 1 mM EDTA), 0.1% (w/v) Ficoll, 0.1% polyvinylpyrrolidine, 0.1% (w/v) BSA, 0.5% SDS, and 200 μg/ml denatured, fragmented salmon sperm DNA for 7 h at 68° C. and hybridized with $2 \times 10^5$ cpm of $^{32}$P-labeled Hif-4c fragment in 4×SET, 0.02% (w/v) Ficoll, 0.02% polyvinylpyrrolidine, 0.02% w/v BSA, 0.5% SDS and 200 μg/ml denatured salmon sperm DNA at 68° C. for 16 h. The filter was rinsed with SET-0.5% SDS at room temperature, washed with 2×SET-0.5% SDS for 5 h at 68° C., replacing the solution once, and with 3 mM Trizma base at room temperature for 4 h, replacing the solution once. After drying the filter, an x-ray film was exposed to the filter for 80 h using a screen. Three colonies gave a strong positive response, namely λ-III-7D, λ-III-2H and λ-III-4C, and 2 colonies a weak one, namely λ-III-1E, λ-III-3D.

Small cultures were prepared from the Hif-4c related clones, Form I DNA was purified, cleaved with Pst I and analyzed by agarose gel electrophoresis as described above. All Form I DNAs gave rise to a large fragment (plasmid pBR322 moiety) and a small one (hybrid insert). The recombinant DNA molecule from λ-III-2H released the largest insert, namely about 900 b.p. This recombinant DNA molecule was designated Z-pBR322(Pst)/HcIF-2H ("Hif-2H") and its insert "Hif-2H fragment".

Hif-2H was tested for its capacity to bind IFmRNA by binding it to DPT paper (4 µg/100 mm²) and hybridizing it to poly(A) RNA (0.3 µg/µl), all as described above, for 16 h and determining IFmRNA activity:

| DNA sample | IF activity (IU/ml)* |
|---|---|
| Hif-2H | 250 ± 50 (average of 4 determinations) |
| Z-pBR322(H3)/Rc β G-4.13 | 30 (average of 2 determinations) |
| pBR322 | 20 |

*Assayed by cytopathic effect reduction.

Hif-2H was recloned as described for Hif-4C and designated Hif-2H.

In a further experiment an additional set of *E. coli* clones containing recombinant DNA molecules was prepared and colonies hybridizing to the labeled Hif-4c fragment were identified. In order to ensure a high yield of plasmids with long cDNA inserts, part of the double-stranded ³²P-labeled leukocyte cDNA prepared enzymatically from leukocyte poly(A) RNA (the same cDNA preparation as described above) was fractionated by size by centrifuging through a sucrose density gradient, using the same procedure described for the centrifugation of the poly(A) RNA. The fractions containing the cDNA with a sedimentation velocity corresponding to a 600 b.p. DNA fragment or greater were pooled and the cDNA recovered after ethanol precipitation. The cDNA was elongated with dCMP residues, hybridized to dGMP-elongated Pst I-cleaved pBR322 and the hybrid DNA used to transform *E. coli* as before, except that *E. coli* HB101 was used. The bacteria were distributed onto 8-cm diameter Millipore filters, placed on Tryptone medium agar plates (containing 10 µg/ml tetracycline) and grown until small colonies appeared. A replica filter was prepared by pressing a fresh, moist Millipore filter onto the colony-bearing filter, peeling it off, placing it face upward on an agar plate containing 4.4% glycerol and incubating it until small colonies appeared. This colony-bearing filter was covered with a further Millipore filter, frozen at −55° C. and stored (D. Hanahan and M. Meselson, "A Protocol For High Density Plasmid Screening", Sept. 1978, personal communication). Eighteen filters, bearing a total of about 5000 colonies were prepared. One replica of each filter was used for hybridization to the ³²P-labeled, Pst I-excised Hif-4c DNA fragment, exactly as described above. About 185 positive colonies were identified on an autoradiogram, recloned on Millipore filters and identified once more by hybridization. 95 clones giving the strongest hybridization response were designated Z-pBR322(Pst)/HcIF-SN1 to SN95 and used for further investigation.

It is, of course, evident that this method of clone screening may be employed equally well on other clones containing DNA sequences arising from recombinant DNA technology, synthesis, natural sources or a combination thereof or clones containing DNA sequences related to any of the above DNA sequences by mutation, including single or multiple, base substitutions, insertions, inversions, or deletions. Therefore, such DNA sequences and their identification also fall within this invention. It is also to be understood that DNA sequences, which are not screened by the above DNA sequences, yet which as a result of their arrangement of nucleotides code on expression for the polypeptides coded for by the expression of the above DNA sequences also fall within this invention.

FURTHER CHARACTERIZATION OF Hif-2h DNA INSERT

As described above recombinant DNA molecule Hif-2h contains an insert of about 900 b.p., and hybridizes to human leukocyte mRNA. The following additional characteristics were determined.

1. Hybrid Arrested Translation

If mRNA is hybridized to a cloned, complementary cDNA, the translation of the mRNA is inhibited, however heat denaturation of the hybrid releases translatable mRNA (B. M. Paterson et al., "Structural Gene Identification And Mapping By DNA-mRNA Hybrid-Arrested Cell-Free Translation", *Proc. Nat'l. Acad. Sci. USA*, 74, pp. 4370–74 (1977)). 2.2 µg Pst I-cleaved Hif-2h, and as a control 2 µg HindIII cleaved Z-pBR322(H3)/Rc β G-4.13 ("Rc β G") were denatured in 10 µl 80% (vol/vol) deionized formamide-20 mM PIPES buffer (pH 6.4) for 10 min at 80° C. The solution was added to an Eppendorf tube into which leukocyte poly(A) RNA (5 µg), NaCl (4 µmoles) and EDTA (10 nmoles) had been dried down. The mixture was heated for 7 h at 48° C. under a layer of paraffin oil, cooled and diluted with 200 µl H₂O. The two samples were divided into equal parts, and one of each was heated at 100° C. for 30 sec. The nucleic acids were precipitated with ethanol, dissolved in 3 µl H₂O and assayed for IFmRNA activity in oocytes as above:

| DNA | Le poly(A) RNA input | Treatment | IF (IU/ml)* |
|---|---|---|---|
| Hif-2h (1.1 µg) | 2.5 µg | hybridized | 400 |
| Hif-2h (1.1 µg) | 2.5 µg | hybridized and denatured | 2000 |
| RcβG (1 µg) | 2.5 µg | hybridized | 3000 |
| RcβG (1 µg) | 2.5 µg | hybridized and denatured | 3000 |
| Hif-2h (0.5 µg) | 1 µg | none | 2000 |
| — | 1 µg | none | 3000 |
| — | 1 µg | none | 2000 |

*The oocyte medium was assayed after 48 h by the cytopathic effect inhibition method.

Therefore, Hif-2h, when hybridized with poly(A) RNA, inhibited the translation of the IFmRNA in the poly(A) RNA; after denaturing the hybrid IFmRNA was again translatable. This experiment confirms that Hif-2h contains sequences complementary to Le IFmRNA.

2. Analysis By Restriction Enzyme Cleavage

Digestions of Hif-2h with various restriction enzymes (New England Biolab) were carried out, and the resulting products analyzed by agarose gel electrophoresis.

The underlined fragments are not common to pBR322 and Hif-2h:

|  | Fragment sizes | |
| --- | --- | --- |
| Restriction enzyme | Hif-2h | pBR322* |
| PstI | 885 ± 20,4361 | 4361 |
| EcoRI | 1426,3820 | 4361 |
| BglII | 5246 | not cleaved |
| EcoRI + BglII | 336,4960 | 4361 |
| EcoRI + PstI | 209,676,748 3611 | 748,3611 |
| BspI | 921,587,540,504, 457,434,2 × 231, +14 fragments <200 bp | 587,540, 504,457, 434,267, 234 +14 fragments <200 bp |
| MboII | 1616,884 and others | not done |

*from Sutcliffe (supra)

In addition, 5' terminally $^{32}$P-labeled PstI cleaved Hif-2h was cleaved with several restriction enzymes and the sizes of the radioactive fragments derived from the cDNA insert in that recombinant DNA molecule were determined:

| Restriction enzyme | $^{32}$P-fragments |
| --- | --- |
| EcoRI | 676,209 |
| HindIII | no cleavage |
| BspI | 799,86 |
| HpaII | no cleavage |
| HhaI | no cleavage |
| BamHI | no cleavage |
| Hinf | 210,62 |
| BglII | 545,340 |

Figure 4:
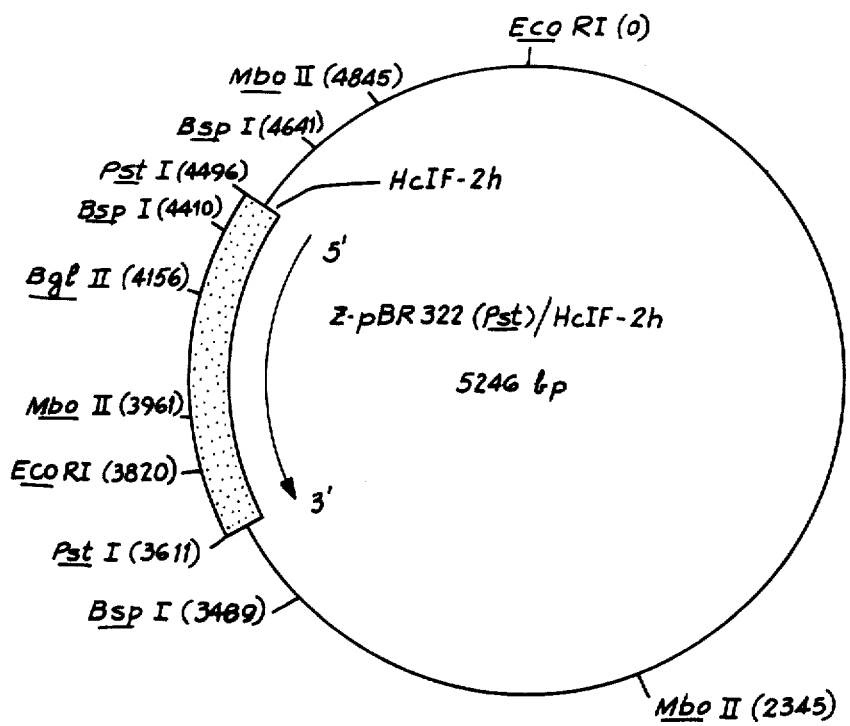
FIG. 4 is a restriction map of one of the clones of the invention. The positions of the restriction sites are based on fragment sizing by agarose gel electrophoresis.

From these data a restriction map of Hif-2h was deduced (FIG. 4). The positions of the restriction sites in FIG. 4 are based on fragment sizing by agarose gel electrophoresis and may also be incomplete in regard to MboII sites within the insert. Only the sites closest to the insert are given within the pBR322 moiety. The arrow indicates the orientation of the IFcDNA coding strand.

3. Determination Of The Plus Strand Of The Inserted IFcDNA

Figure 5:
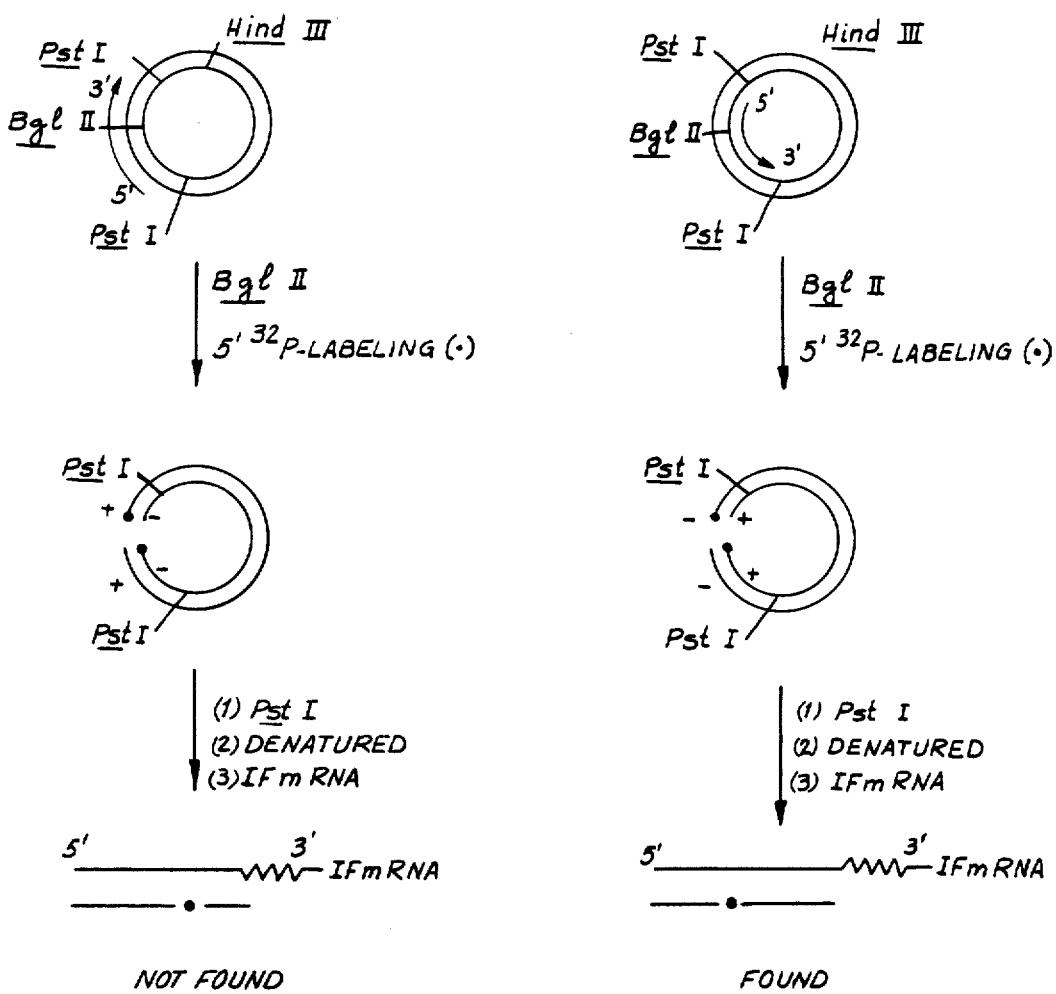
FIG. 5 is a schematic outline of the process of determining the orientation of a DNA insert in one recombinant DNA molecule of this invention.

The DNA strand that has the same sequence as the mRNA is designated as plus strand, and its complement as minus strand. The plus strand of the IFcDNA insert was identified as outlined in FIG. 5. Hif-2h DNA was cleaved with the restriction enzyme BglII, the termini labeled with $^{32}$P-phosphate (as described above for PstI-cleaved termini) and the DNA digested with PstI, to give a longer (545 b.p.) and a shorter (340 b.p.) radioactive fragment. These fragments were denatured and hybridized to poly(A) RNA from induced leukocytes in 80% formamide, 0.4M NaCl, i.e., under conditions where DNA-DNA reassociation does not occur (supra). The nucleic acids were digested with nuclease S1, which degrades all single-stranded nucleic acids, in particular the non-hybridized $^{32}$P-DNA, and the products were separated on a polyacrylamide gel (R. F. Weaver and C. Weissmann, "Mapping Of RNA By A Modification of The Berk-Sharp Procedure", Nucleic Acid Research, 7, pp. 1175-93 (1979)). An autoradiogram showed that only the shorter 340-nucleotide fragment had been hybridized and protected by the poly(A) RNA, identifying the 5'-labeled 340-nucleotide strand as the minus strand. The orientation of the plus strand is therefore as given in FIG. 4 and FIG. 5 (right hand side).

4. Demonstration That Poly(A) RNA From Non-Induced Human Leukocytes Does Not Hybridize To Hif-2H DNA An experiment identical to that described in the preceding section was carried out, however the poly(A) RNA was from non-induced human leukocytes, prepared by the same procedure as in the case of Sendai virus-induced leukocytes. No detectable amount of labeled DNA was protected; by comparison to the results of the preceding section the poly(A) RNA from non-induced cells contains less than about 1/20 the amount of mRNA hybridizable to Hif-2h than does poly(A) RNA from induced cells.

SYNTHESIS OF A POLYPEPTIDE WITH INTERFERON ACTIVITY BY E. COLI CONTAINING RECOMBINANT DNA MOLECULES RELATED TO Z-pBR322(Pst)/HcIF-4c

The PstI site of pBR322 lies within the β-lactamase (penicillinase) gene. Therefore, when a coding DNA segment (e.g., a cDNA comprising all or part of a gene) is ligated into the position in the proper orientation and proper reading frame, a fused protein may result, consisting of the amino-terminal portion of β-lactamase followed by the amino acid sequence for which the inserted DNA sequence codes (L. Villa-Komaroff et al., supra). If the inserted DNA segment comprises a DNA sequence containing its own initiation signal, and has a sequence preceding it with a termination signal in phase with the β-lactamase sequence, initiation may occur at the initiation signal and a non-fused, active protein may result (A.C.Y. Chang et al., supra). To ensure that the DNA insert related to Hif-4c was inserted in the proper reading frame for expression within the β-lactamase gene, a set of derivatives of pBR322, namely pKT279, pKT280 and pKT287, (constructed by K. Talmadge, personal communication, 1979) was employed. Each of these derivatives has a PstI site located such that a DNA insert ligated into that site will be in a different reading frame from an insert at the PstI site of the other derivatives of the set (FIG. 6). Therefore, the set permits the insertion of DNA into the β-lactamase gene in all three reading frames. The PstI-excised insert from Hif-2h was prepared as described for the fragment Hif-4c. The Hif-2h Pst fragment (10 ng) was mixed with PstI-cleaved pBR322, pKT279, pKT280 or pKT287 (10 ng in each case) in 20 μl of 10 mM Tris-HCl (pH 7.5), 6 mM MgCl$_2$, 100 mM NaCl, 6 mM β-mercaptoethanol, 200 μg/ml gelatin and 0.1 mM ATP and incubated with 0.1 units T$_4$ DNA ligase (New England Biolabs) for 16 h at 10° C. The resulting recombinant DNA molecules are designated Z-pBR322(Pst)/HcIF-2h, Z-pKT279(Pst)/HcIF-2h, Z-pKT280(Pst)/HcIF-2h and Z-pKT287(Pst)/HcIF-2h. E. coli HB101 was transformed with each of these recombinant DNA molecules and transformed colonies were selected on tetracycline-containing agar plates as described previously. Since tetracycline-resistant clones of transformed bacteria may also contain the recyclized vector, bacterial colonies of each set were grown on Millipore filters and colonies hybridizing to $^{32}$P-labeled Hif-4c fragment were identified and selected as described above. These strains were designated as follows, E. coli HB101 (Z-pBR322(Pst)/HcIF-2h-AH1) to (-AH3);

E. coli HB101 (Z-pKT279(Pst)/HcIF-2h-AH1) to (-AH8);

E. coli HB101 (Z-pKT280(Pst)/HcIF-2h-AH1) to (-AH8);

E. coli HB101 (Z-pKT287(Pst)/HcIF-2h-AH1) to (-AH8).

Extracts of some of the above strains as well as of some of the strains Z-pBR322(Pst)/HcIF-SN1 to 95 were tested for IF activity. Bacteria were grown in Tryptone medium to stationary phase, harvested, washed with 1/20 of the vol of the culture of 50 mM Tris-HCl (pH 8) 30 mM NaCl and frozen. After thawing, the cells were resuspended in the volume indicated below of the previous buffer and lysozyme was added to 1 mg/ml. After 60 min at 0° C. the suspensions were frozen (in an ethanol-dry ice bath) and thawed (at 37° C.) 5 times, and centrifuged 10 min at 12,000 rpm in a GSA Sorvall rotor. In some cases part of the supernatant (S30) was further centrifuged at 100,000 xg in a Type 65 Spinco rotor and the supernatants (S100) recovered. Such supernatants were screened for IF activity by the cytopathic effect reduction assay (Expt. 1). The colonies showing a positive response in Expt. 1 were reassayed as well as 49 clones from the set Z-pBR322/HcIF-SN-1 to SN-95 described above at a lower dilution (Expt. 2).

| Source of Extract E. coli HB101 transformed by: | Preparation | IF activity (IU/ml) |
|---|---|---|
| Expt. 1* | | |
| Z-pBR322(Pst)/HcIF-2h | S30 | ? |
| Z-pBR322(Pst)/HcIF-2h-AH-1 to 3 | S30 | ? |
| Z-pKT279(Pst)/HcIF-2h-AH-1 to 7 | S30 | ? |
| Z-pKT279(Pst)/HcIF-2h-AH-8 | S30 | pos |
| Z-pKT280(Pst)/HcIF-2h-AH-2,6,7 | S30 | ? |
| Z-pKT280(Pst)/HcIF-2h-AH-1,3,4,5 | S30 | pos |
| Z-pKT287(Pst)/HcIF-2h-AH-1,2,3,4,5,8 | S30 | ? |
| Z-pKT287(Pst)/HcIF-2h-AH-6,7 | S30 | pos |
| Expt. 2* | | |
| Z-pKT279/HcIF-2h-AH-8 | S30 and S100 | 300 |
| Z-pKT280/HcIF-2h-AH-1,3,4,5 | S30 and S100 | 300 |
| Z-pKT287/HcIF-2h-AH-6 and 7 | S30 and S100 | 300 |
| Z-pBR322(Pst)/HcIF-SN-4,5,7,9,10,11,13, to 16 | S30 | neg (<10) |
| Z-pBR322(Pst)/HcIF-SN-18 to 22, 24,25,27, 30 to 34 | S30 | neg (<10) |
| Z-pBR322(Pst)/HcIF-SN-38 to 41, 43 to 48 | S30 | neg (<10) |
| Z-pBR322(Pst)/HcIF-SN-1 to 3,6, 8,12,17, 23,26 | S30 | 10 |
| Z-pBR322(Pst)/HcIF-SN-28,29,36, 37,49 | S30 | 10 |
| Z-pBR322(Pst)/HcIF-SN-35,42 | S30 | 200 |

*Expt. 1: Extracts assayed at 1:150 final dilution
*Expt. 2: Extracts assayed at 1:6 final dilution Some of the more active producers from above were examined in more detail. Cultures were grown to late log phase (apparent OD$_{650}$ about 0.9) and the cells lysed as above, in 1/50 of the culture volume. The following activities were found, using Z-pBR322(Pst)/HcIF-SN 32 as a negative control:

| Source of extract: E. coli HB101 transformed by: | Preparation | IF activity (IU/ml) (dup. assays) |
|---|---|---|
| Z-pKT279(Pst)/HcIF-2h-AH8 | S30, S100 | 100; 300 |
| Z-pKT280(Pst)/HcIF-2h-AH3 | S30, S100 | 1000; 1000 |
| Z-pKT287(Pst)/HcIF-2h-AH6 | S30, S100 | 200; 200 |
| Z-pBR322(Pst)/HcIF-SN35 | S30, S100 | 1000; 1000 |
| Z-pBR322(Pst)/HcIF-SN42 | S30, S100 | 300; 100 |
| Z-pBR322(Pst)/HcIF-SN32 | S30, S100 | 0; 0 |

It is of course to be understood, that the above results may reflect interferon production by genes under the control of the penicillinase expression control sequence. As is known in the art, expression levels may be improved in several ways.

The level of production of a protein is governed by two major factors: the number of copies of its gene within the cell and the efficiency with which those gene copies are transcribed and translated. Efficiency of transcription and translation (which together comprise expression) is in turn dependent upon nucleotide sequences, normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and fuse them instead to other known expression control sequences so as to favor higher levels of expression. This having been achieved, the newly engineered DNA fragment may be inserted into a multicopy plasmid or a bacteriophage derivative in order to increase the number of gene copies within the cell and thereby further improve the yield of expressed protein.

Several expression control sequences may be employed as described above. These include the operator, promoter and ribosome binding and interaction sequences (including sequences such as the Shine-Dalgarno sequences) of the lactose operon of E. coli ("the lac system"), the corresponding sequences of the tryptophan synthetase system of E. coli ("the trp system"), the major operator and promoter regions of phage λ ($O_L P_L$ and $O_R P_R'$), the control region of the phage fd coat protein, or other sequences which control the expression of genes of prokaryotic or eukaryotic cells and their viruses. Therefore, to improve the production of a particular polypeptide in an appropriate host, the gene coding for that polypeptide may be prepared as before and removed from a recombinant DNA molecule containing it and reinserted into a recombinant DNA molecule closer to its former expression control sequence or under the control of one of the above expression control sequences. Such methods are known in the art.

Further increases in the cellular yield of the desired products depend upon an increase in the number of genes that can be utilized in the cell. This is achieved, for illustration purposes, by insertion of recombinant DNA molecules engineered in the way described previously into the temperate bacteriophage λ (NM989), most simply by digestion of the plasmid with a restriction enzyme, to give a linear molecule which is then mixed with a restricted phage λ cloning vehicle (e.g., of the type described by N. E. Murray et al., "Lambdoid Phages That Simplify The Recovery Of In Vitro Recombinants", *Molec. gen. Genet.* 150, pp. 53–61 (1977) and N. E. Murray et al., "Molecular Cloning Of The DNA Ligase Gene From Bacteriophage T4", *J. Mol. Biol.*, 132, pp. 493–505 (1979)) and the recombinant DNA molecule produced by incubation with DNA ligase. The desired recombinant phage is then selected as before and used to lysogenise a host strain of *E. coli.*

Particularly useful λ cloning vehicles contain a temperature-sensitive mutation in the repression gene cI and suppressible mutations in gene S, the product of which is necessary for lysis of the host cell, and gene E, the product which is the major capsid protein of the virus. With this system the lysogenic cells are grown at 32° C. and then heated to 45° C. to induce excision of the prophage. Prolonged growth at 37° C. leads to high levels of production of the protein, which is retained within the cells, since these are not lysed by phage gene products in the normal way, and since the phage gene insert is not encapsidated it remains available for further transcription. Artificial lysis of the cells then releases the desired product in high yield.

PROPERTIES OF INTERFERON ACTIVITY PRODUCED BY *E. COLI* TRANSFORMED WITH HYBRID PLASMIDS

1. Sensitivity Of IF Activity To Trypsin

50 μl samples of authentic human leukocyte IF (specific activity, $1.2 \times 10^6$ U/mg; 50U), and the S100 extracts described above of *E. coli* HB101 (Z-pKT287(Pst)/HcIF-2h-AH6) ("Hif-287-6 extracts") (200 U/ml, 10 U) and of *E. coli* HB101 (Z-pBR322(Pst)/HcIF-SN35) ("Hif-35 extracts") (1000 U/ml; 50 U) were incubated with various amounts of trypsin, as indicated, for 30 min at 37° C. Since the S100 extracts have a high protein content, while the Le IF does not, a mixture of Le IF and the control S100 extract Hif-32 was tested in parallel:

| IF preparation | Trypsin μ(g) | IF activity (units) |
|---|---|---|
| Human Le IF (50 units in 50 μl Hif-32 S100 extract) | 0 | 50 |
| | 0.1 | 50 |
| | 1 | 50 |
| | 10 | 5 |
| | 50 | 0 |
| Hif-287-6 S100 extract (10 units) | 0 | 15 |
| | 0.1 | 15 |
| | 1 | 5 |
| | 10 | 1 |
| | 50 | 0 |
| Hif-35 S100 extract (50 units) | 0 | 30 |
| | 0.1 | 20 |
| | 1 | 20 |
| | 10 | 2 |
| | 50 | 0 |

2. Behavior On Chromatorgraphy On Sephadex G-100

Extracts Hif-35 (1 ml) and the S100 extract of *E. coli* HB101 (Z-pBR322(Pst)/HcIF-SN32) ("Hif-32 extracts") were chromatographed on a 32-ml Sephadex G-100 column at 4° C. in 50 mM K-phosphate buffer (pH 7.4). Cytochrome c (0.2 mg) was added as an internal marker. The flow rate was 2 ml/hr and 1.0 ml fractions were collected. The absorbance at 280 nm, and 405 nm (cytochrome c), and the IF activity were determined. As shown in FIG. 7, the IF activity of Hif-35 extracts was eluted before cytochrome c, with a $k_D$ value of about 0.45. Therefore, the apparent molecular weight of the substance was between about 20,000 and 30,000; no activity was detected in the fractions of control extract Hif-32.

3. Inhibition Of The Interferon Activity of Hif-35 And Hif-287-6 By Antibody Against Human Leukocyte Interferon Human Le IF (specific activity $1.2 \times 10^6$ IU/mg), and the Hif-35/Hif-287-6 S100 extracts were incubated with various dilutions of sheep antiserum against human Le IF (prep. K. Cantell, Feb. 24, 1976, specific activity 450,000 units/ml) in 100 μl Modified Eagles Medium (MEM) with 10% calf serum for 30 min at 37° C. and 45 μl were assayed for IF activity by the cytopathic effect reduction assay. (The antibody itself did not cause a cytopathic effect):

| IF Preparation (units) | Anti-leukocyte-interferon antibody (units) | Residual IF activity (IU) |
|---|---|---|
| Leukocyte interferon (10) | 0 | 5 |
| | 0.18 | ~0.5 |
| | 9 | <0.1 |
| | 450 | <0.1 |
| Hif-35 extract (25) | 0 | 15 |
| | 0.18 | 15 |
| | 9 | <0.1 |
| | 450 | <0.1 |
| Hif-287-6 extract (25) | 0 | 15 |
| | 0.18 | 15 |
| | 9 | <0.1 |
| | 450 | <0.1 |
| none | 0 | <0.1 |
| | 450 | <0.1 |

To show that the action of the antibody was not due to an unspecific effect, such as proteolytic degradation, a similar experiment was performed with the mouse interferon system:

| IF Preparation (Units) | Anti-leukocyte-interferon antibody (units/ml) | IF activity (units/ml) mouse system |
|---|---|---|
| mouse preparation (100 units) | 4500 | 100 |
| | 90 | 100 |
| | 18 | 100 |

Thus, antibodies directed against human Le IF specifically inhibit the IF activity of polypeptides produced in *E. coli* transformed with certain recombinant DNA molecules containing the HcIF-2h DNA sequence. The apparently lower affinity of the antibody for the IF produced in *E. coli* may reflect structural difference between the latter and natural Le IF, for example, absence of carbohydrate moiety, presence of signal sequence, or fusion to part of the β-lactamase sequence.

4. Reduced Activity of Hif-35 And Hif-287-6 Extracts On Mouse Cells

Human CCL23 cells or Mouse L929 cells were treated with *E. coli* extracts, human leukocyte IF (prep., K. Cantell, specific activity $1.2 \times 10^6$ units/mg) or mouse IF (N.I.H. standard), were challenged with virus (Mengo virus in the case of human cells and VSV in the case of mouse cells) and the IF activity determined by the cytopathic effect reduction assay:

| Addition | IF activity (units/ml) | |
|---|---|---|
| | human system | mouse system |
| mouse - interferon (120 units/ml) | — | 120 |
| Hif-35 extracts | 100 | 13 |
| | 1000 | 120 |
| Hif-287-6 extracts | 30 | 4 |
| | 300 | 40 |
| human interferon (100 units/ml) | 100 | 4 |
| human interferon (1000 units/ml) | 1000 | 40 |

These results show that Hif-35 and Hif-287-6 extracts have a protective action on human cells and only a slight effect (~10%) on mouse cells, as is typical for human interferon.

FINAL CONCLUSIONS

We have isolated a set of recombinant DNA molecules containing cDNA prepared from poly(A) RNA from Sendai virus-treated (induced) human leukocytes, representatives of which have the following properties:

(1) They hybridize to poly(A) RNA from induced but not from non-induced human leukocytes.

(2) They hybridize to leukocyte interferon mRNA as shown by their capacity to select this RNA from a mixture of RNAs, and by their capacity to inhibit (reversibly) translation of interferon mRNA in the hybrid arrested translation assay.

(3) E. coli containing certain members of the set produce a compound with the following properties:

(a) It is sensitive to trypsin (b) It exhibits IF activity in a human cell system and only slight activity in a mouse cell system (c) It has a molecular weight between 20,000 and 30,000

(d) The IF activity is specifically inhibited by antibody to human leukocyte interferon.

These properties demonstrate that the recombinant DNA molecules described by this invention contain at least a part of the coding sequence for human leukocyte interferon and that some of these plasmids led to expression in E. coli of a polypeptide with an immunological or biological activity of human leukocyte interferon. It should also be evident that the polypeptides disclosed herein may be fragmented, modified or derivatized, as is well known in the protein art, without departing from the scope or disclosure of this invention.

Micro-organisms and recombinant DNA molecules prepared by the processes described herein are exemplified by cultures deposited in the culture collection Deutsche Sammlung von Mikroorganismen, in Gottingen, West Germany on Jan. 7, 1980, and identified as HcIF-A to E:

A. E. coli HB101 (Z-pBR322(Pst)/HcIF-4c)
B: E. coli HB101 (Z-pBR322(Pst)/HcIF-2h)
C: E. coli HB101 (Z-pBR322(Pst)/HcIF-SN35)
D: E. coli HB101 (Z-pBR322(Pst)/HcIF-SN42)
E: E. coli HB101 (Z-pKT287(Pst)/HcIF-2h-AH6)

These cultures were assigned accession numbers DSM 1699–1703, respectively.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than the specific embodiments which have been presented hereinbefore by way of example.

I claim:

1. A recombinant DNA molecule consisting of segments of DNA from different genomes which have been joined end-to-end outside of living cells and which have the capacity to infect some host and to be maintained therein, and the progeny thereof, comprising a DNA sequence selected from the group consisting of:

(a) the DNA inserts of Z-pBR322(Pst)/HcIF-2h (DSM 1700), Z-pBR322(Pst)/HcIF-SN35 (DSM 1701), Z-pBR322(Pst)/HcIF-SN42 (DSM 1702) and Z-pKT287(Pst)/HcIF-2h-AH6 (DSM 1703), (b) DNA sequences which hybridize to any of the foregoing DNA inserts and which code on expression for a polypeptide of the IFN-α type, and (c) DNA sequences which code on expression for a polypeptide of the IFN-α type coded for on expression by any of the foregoing DNA sequences and inserts, said DNA sequences and inserts being operatively linked to an expression control sequence in said recombinant DNA molecule.

2. The recombinant DNA molecule according to claim 1, wherein the molecule comprises a cloning vehicle having at least one restriction endonuclease recognition site, said DNA sequence being inserted at one of said recognition sites or between two of such sites.

3. The recombinant DNA molecule according to claim 2, wherein the expression control sequence is also inserted into the cloning vehicle.

4. The recombinant DNA molecule according to claim 1, wherein the expression control sequence is selected from the group consisting of a lac system, a trp system, major operator and promoter regions of phage λ, the control region of fd coat protein, and other sequences which control the expression of genes of prokaryotic or eukaryotic cells and their viruses.

5. A unicellular host transformed with at least one recombinant DNA molecule, said molecule, consisting of segments of DNA from different genomes which have been joined end-to-end outside of living cells and which have the capacity to infect some host and to be maintained therein, and the progeny thereof, comprising a DNA sequence selected from the group consisting of:

(a) the DNA inserts of Z-pBR322(Pst)/HcIF-4c (DMS 1699), Z-pBR322(Pst)/HcIF-2h (DSM 1700), Z-pBR322(Pst)/HcIF-SN35 (DSM 1701), Z-pBR322(Pst)/HcIF-SN42 (DSM 1702) and Z-pKT287(Pst)/HcIF-2h-AH6 (DSM 1703), (b) DNA sequences which hybridize to any of the foregoing DNA inserts and which code on expression for a polypeptide of the IFN-α type, and (c) DNA sequences which code on expression for a polypeptide of the IFN-α type coded for on expression by any of the foregoing DNA sequences and inserts.

6. The transformed host according to claim 5, wherein said DNA sequence is operatively linked to an expression control sequence.

7. The transformed host according to claim 5, wherein the host is selected from the group consisting of E. coli HB101 (Z-pBR322(Pst)/HcIF-4c) (DSM 1699), E. coli HB101 (Z-pBR322(Pst)/HcIF-2h) (DSM 1700), E. coli HB101 (Z-pBR322(Pst)/HcIF-SN35) (DSM 1701), E. coli HB101 (Z-pBR322(Pst)/HcIF- SN42) (DSM 1702) and *E. coli* HB101 (Z-pKT287(Pst)/HcIF-2h-AH6) (DSM 1703).

8. A substantially pure DNA sequence selected from the group consisting of:
  (a) the DNA inserts of Z-pBR322(Pst)/HcIF-4c (DSM 1699), Z-pBR322(Pst)/HcIF-2h (DSM 1700), Z-pBR322(Pst)/HcIF-SN35 (DSM 1701), Z-pBR322(Pst)/HcIF-SN42 (DSM 1702) and Z-pKT287(Pst)/HcIF-2h-AH6 (DSM 1703),
  (b) DNA sequences which hybridize to any of the foregoing DNA inserts and which code on expression for a polypeptide of the IFN-α type, and
  (c) DNA sequences which code on expression for a polypeptide of the IFN-α type coded for on expression by any of the foregoing DNA sequences and inserts, said DNA sequences coding on expression for only a single polypeptide chain.

9. A method for producing a polypeptide comprising the steps of preparing a recombinant DNA molecule, consisting of segments of DNA from different genomes which have been joined end-to-end outside of living cells and which have the capacity to infect some host and to be maintained therein, and the progeny thereof, comprising a DNA sequence selected from the group consisting of:
  (a) the DNA inserts of Z-pBR322(Pst)/HcIF-2h (DSM 1700), Z-pBR322(Pst)/HcIF-SN35 (DSM 1701), Z-pBR322(Pst)/HcIF-SN42 (DSM 1702) and Z-pKT287(Pst)/HcIF-2h-AH6 (DSM 1703),
  (b) DNA sequences which hybridize to any of the foregoing DNA inserts and which code on expression for a polypeptide of the IFN-α type, and
  (c) DNA sequences which code on expression for a polypeptide of the IFN-α type coded for on expression by any of the foregoing DNA sequences or inserts, and having operatively linked thereto an expression control sequence; transforming an appropriate host with said recombinant DNA molecule; culturing said host; and collecting said polypeptide.

10. The method according to claim 9, wherein the host is selected from the group consisting of strains of *E. coli*, Pseudomonas, *Bacillus subtilis*, *Bacillus stearothermophilus*, other bacilli, yeasts, other fungi, animal and plant hosts, and human tissue cells.

11. The method according to claim 9, wherein the expression control sequence is selected from the group consisting of the lac system, the trp system, the major operator and promoter region of phage λ, the control region of fd coat protein, and other sequences which control the expression of genes of prokaryotic or eukaryotic cells and their viruses.

12. A method for producing a polypeptide comprising the steps of culturing a host transformed with a recombinant DNA molecule, consisting of segments of DNA from different genomes which have been joined end-to-end outside of living cells and which have the capacity to infect some host and to be maintained therein, and the progeny thereof, comprising a DNA sequence selected from the group consisting of:
  (a) the DNA inserts of Z-pBR322(Pst)/HcIF-2h (DSM 1700), Z-pBR322(Pst)/HcIF-SN35 (DSM 1701), Z-pBR322(Pst)/HcIF-SN42 (DSM 1702) and Z-pKT287(Pst)/HcIF-2h-AH6 (DSM 1703),
  (b) DNA sequences which hybridize to any of the foregoing DNA inserts and which code on expression for a polypeptide of the IFN-α type, and
  (c) DNA sequences which code on expression for a polypeptide of the IFN-α type coded for on expression by any of the foregoing DNA sequences and inserts, and having operatively linked thereto an expression control sequence; and collecting said polypeptide.

13. The method according to claim 12, wherein the host is selected from the group consisting of strains of *E. coli*, Pseudomonas, *Bacillus subtilis*, *Bacillus stearothermophilus*, other bacilli, yeasts, other fungi, animal and plant hosts, and human tissue cells.

14. The method according to claim 12, wherein the expression control sequence is selected from the group consisting of the lac system, the trp system, the major operator and promoter region of phage λ, the control region of fd coat protein, and other sequences which control the expression of genes of prokaryotic or eukaryotic cells and their viruses.

15. The transformed host according to claim 6, wherein the host is selected from the group consisting of strains of *E. coli*, Pseudomonas, *Bacillus subtilis*, *Bacillus stearothermophilus*, other bacilli, yeasts, other fungi, animal and plant hosts, and human tissue cells.

16. The transformed host according to claim 1, wherein the host is a microorganism.

17. The recombinant DNA molecule according to claim 1, wherein said molecule is selected from the group consisting of plasmids and phages.

18. The method according to claim 9 or 12, wherein said recombinant DNA molecule is selected from the group consisting of plasmids and phages.

* * * * *

UNITED STATES PATENT AND TRADEMARK OFFICE
CERTIFICATE OF CORRECTION

PATENT NO. : 4,530,901
DATED : July 23, 1985
INVENTOR(S) : Charles Weissmann

It is certified that error appears in the above-identified patent and that said Letters Patent is hereby corrected as shown below:

Cover page, below "OTHER PUBLICATIONS", line 7, "Quarterly Rev. Biol. 446, 111 (1971)" should be --Quarterly Rev. Biol. 46, 111 (1971)--.

Page 3, below "ABSTRACT", line 8, "immulogical" should be --immunological--.

Column 6, line 25, "Neucleotide" should be --Nucleotide--.

Column 12, line 56, "molecular" should be --molecule--.

Column 14, line 22, "ane" should be --and--.

Column 18, line 7, "12 82 g" should be --12 $\mu$g--.

Column 26, line 47, "=P-" shoud be --$^{32}$P--.

Column 33, line 59, "Chromatorgraphy" should be --Chromatography--.

Column 38, line 42, "claim 1" should be --claim 6--.

Signed and Sealed this

Fifth Day of July, 1988

Attest:

DONALD J. QUIGG

Attesting Officer

Commissioner of Patents and Trademarks